United States Patent
Burba, III et al.

(10) Patent No.: US 8,252,087 B2
(45) Date of Patent: Aug. 28, 2012

(54) PROCESS AND APPARATUS FOR TREATING A GAS CONTAINING A CONTAMINANT

(75) Inventors: John L. Burba, III, Parker, CO (US); Tim L. Oriard, Issaquah, WA (US)

(73) Assignee: Molycorp Minerals, LLC, Greenwood Village, CO (US)

( * ) Notice: Subject to any disclaimer, the term of this patent is extended or adjusted under 35 U.S.C. 154(b) by 242 days.

(21) Appl. No.: 11/932,090

(22) Filed: Oct. 31, 2007

(65) Prior Publication Data

US 2009/0112043 A1    Apr. 30, 2009

(51) Int. Cl.
   *B01D 53/02* (2006.01)
(52) U.S. Cl. ............... 95/8; 95/21; 423/230; 423/239.1; 423/240 S; 423/244.01; 588/299; 588/400
(58) Field of Classification Search ............ 95/116, 95/127–147, 900, 148, 8, 11, 14, 19, 21; 423/230, 239.1, 240 S, 244.01, 245.1, 263; 588/299, 315, 320, 400, 402, 403, 405
See application file for complete search history.

(56) References Cited

U.S. PATENT DOCUMENTS

| | | |
|---|---|---|
| 1,739,840 A | 12/1929 | Kendall |
| 2,564,241 A | 8/1951 | Warf |
| 2,567,661 A | 9/1951 | Ayres |
| 2,847,332 A | 8/1958 | Ramadanoff |
| 2,872,286 A | 2/1959 | Finzel |
| 3,194,629 A | 7/1965 | Dreibelbis et al. |
| 3,259,568 A | 7/1966 | Jordan et al. |
| 3,337,452 A | 8/1967 | Teske et al. |
| 3,347,786 A | 10/1967 | Baer et al. |
| 3,385,915 A | 5/1968 | Hamling |
| 3,575,853 A | 4/1971 | Gaughan et al. |
| 3,617,569 A | 11/1971 | Daniels et al. |
| 3,658,724 A | 4/1972 | Stiles |
| 3,692,671 A | 9/1972 | Recht et al. |
| 3,736,255 A | 5/1973 | Ghassemi et al. |
| 3,761,571 A | 9/1973 | Woodhead |
| 3,768,989 A | 10/1973 | Goetzinger et al. |
| 3,838,759 A | 10/1974 | Schmoelz et al. |
| 3,849,537 A | 11/1974 | Allgulin |
| 3,865,728 A | 2/1975 | Abbott et al. |
| 3,916,585 A | 11/1975 | Barks |
| 3,926,807 A | 12/1975 | Evers et al. |
| 3,956,118 A | 5/1976 | Kleber et al. |
| 3,965,118 A | 6/1976 | Van Rheenen |
| 4,001,375 A | 1/1977 | Longo |
| 4,046,687 A | 9/1977 | Schulze |
| 4,054,516 A | 10/1977 | Izumi et al. |
| 4,059,520 A | 11/1977 | Roller |
| 4,078,058 A | 3/1978 | Fox |
| 4,080,290 A | 3/1978 | Klantschi et al. |
| 4,088,754 A | 5/1978 | Monafo |
| 4,094,777 A | 6/1978 | Sugier et al. |
| 4,096,064 A | 6/1978 | Du Fresne |
| 4,101,631 A | 7/1978 | Ambrosini et al. |
| 4,127,644 A | 11/1978 | Norman et al. |
| 4,145,282 A | 3/1979 | Bruckenstein |
| 4,200,609 A | 4/1980 | Byrd |
| 4,230,682 A | 10/1980 | Bamberger |
| 4,231,893 A | 11/1980 | Woodhead |
| 4,251,496 A | 2/1981 | Longo et al. |
| 4,313,925 A | 2/1982 | Bamberger |
| 4,346,063 A | 8/1982 | Cahn et al. |
| 4,386,063 A | 5/1983 | Boden |
| 4,404,197 A | 9/1983 | Fox et al. |
| 4,436,655 A | 3/1984 | Masotti et al. |
| 4,474,580 A | 10/1984 | Mackenzie et al. |
| 4,474,896 A | 10/1984 | Chao |
| 4,477,315 A | 10/1984 | Tomaszewski |
| 4,498,706 A | 2/1985 | Ilardi et al. |
| 4,507,206 A | 3/1985 | Hughes |
| 4,566,975 A | 1/1986 | Allgulin |
| 4,581,229 A | 4/1986 | Petrow |
| 4,585,583 A | 4/1986 | Roberson et al. |
| 4,588,088 A | 5/1986 | Allen |
| 4,596,659 A | 6/1986 | Nomura et al. |
| 4,622,149 A | 11/1986 | Devuyst et al. |

(Continued)

FOREIGN PATENT DOCUMENTS

| CA | 2396510 | 2/2003 |
|---|---|---|

(Continued)

OTHER PUBLICATIONS

U.S. Appl. No. 11/793,895, filed May 9, 2008, Boen et al.
U.S. Appl. No. 12/610,569, filed Nov. 2, 2009, Witham et al.
U.S. Appl. No. 12/616,653, filed Nov. 11, 2009, Burba et al.
U.S. Appl. No. 12/632,523, filed Dec. 7, 2009, Witham.
Abanades et al., "Thermochemical hydrogen production from a two-step solar-driven water-splitting cycle based on cerium oxides." Solar Energy 80 (2006) 1611-1623.

(Continued)

*Primary Examiner* — Frank Lawrence, Jr.
(74) *Attorney, Agent, or Firm* — Sheridan Ross, P.C.

(57) ABSTRACT

Apparatus, process and article for treating a gas containing one or more of a chemical and/or biological contaminant. The process includes contacting the gas with an aggregate composition comprising an insoluble rare earth-containing compound to form a gas depleted of chemical and active biological contaminants. The insoluble rare earth-containing compound can include one or more of cerium, lanthanum, or praseodymium. The composition comprises no more than two elements selected from the group consisting of yttrium, scandium, and europium when the aggregate has been sintered. A suitable insoluble cerium-containing compound can be derived from cerium carbonate. In one embodiment, the aggregate composition consists essentially of one or more cerium oxides, and optionally, a binder. Although intended for a variety of fluid treatment applications, such applications specifically include the treatment of breathing gases such as air that may contain chemical and/or biological contaminants.

46 Claims, No Drawings

U.S. PATENT DOCUMENTS

| | | | |
|---|---|---|---|
| 4,636,289 A | 1/1987 | Mani et al. | |
| 4,652,054 A | 3/1987 | Copenhafer et al. | |
| 4,661,330 A | 4/1987 | Chane-ching et al. | |
| 4,714,694 A | 12/1987 | Wan et al. | |
| 4,738,799 A | 4/1988 | Troy | |
| 4,753,728 A | 6/1988 | VanderBilt et al. | |
| 4,786,483 A | 11/1988 | Audeh | |
| 4,814,152 A | 3/1989 | Tan | |
| 4,818,483 A | 4/1989 | Culling | |
| 4,828,832 A | 5/1989 | De Cuellar et al. | |
| 4,831,519 A | 5/1989 | Morton | |
| 4,842,898 A | 6/1989 | Gradeff | |
| 4,843,102 A | 6/1989 | Horton | |
| 4,849,223 A | 7/1989 | Pratt | |
| 4,857,280 A * | 8/1989 | Kay et al. | 423/21.1 |
| 4,859,432 A | 8/1989 | David et al. | |
| 4,861,519 A | 8/1989 | Tusa et al. | |
| 4,881,176 A | 11/1989 | Kononov | |
| 4,881,976 A | 11/1989 | Gradeff | |
| 4,889,771 A | 12/1989 | Gradeff et al. | |
| 4,891,067 A | 1/1990 | Rappas et al. | |
| 4,902,426 A | 2/1990 | Macedo et al. | |
| 4,917,875 A | 4/1990 | Moore et al. | |
| 4,920,195 A | 4/1990 | Kankare et al. | |
| 4,935,146 A | 6/1990 | O'Neill et al. | |
| 4,946,592 A | 8/1990 | Galaj et al. | |
| 4,968,322 A | 11/1990 | Miyawaki et al. | |
| 4,973,501 A | 11/1990 | Gradeff | |
| 4,997,425 A | 3/1991 | Shioya et al. | |
| 4,999,174 A * | 3/1991 | Wilson et al. | 423/241 |
| 5,002,747 A | 3/1991 | Le Loarer | |
| 5,004,711 A | 4/1991 | Grodek | |
| 5,013,534 A | 5/1991 | Dissaux et al. | |
| 5,024,769 A | 6/1991 | Gallup | |
| 5,028,736 A | 7/1991 | Girrbach et al. | |
| 5,043,072 A | 8/1991 | Hitotsuyanagi et al. | |
| 5,053,139 A | 10/1991 | Dodwell et al. | |
| 5,061,560 A | 10/1991 | Tajima et al. | |
| 5,064,628 A | 11/1991 | Chane-ching et al. | |
| 5,066,758 A | 11/1991 | Honel et al. | |
| 5,080,926 A | 1/1992 | Porter et al. | |
| 5,082,570 A | 1/1992 | Higgins et al. | |
| 5,104,660 A | 4/1992 | Chvapil et al. | |
| 5,116,418 A | 5/1992 | Kaliski | |
| 5,116,620 A | 5/1992 | Chvapil et al. | |
| 5,126,116 A | 6/1992 | Krause et al. | |
| 5,133,948 A | 7/1992 | King et al. | |
| 5,145,587 A | 9/1992 | Ishii et al. | |
| 5,152,936 A | 10/1992 | Tajima et al. | |
| 5,161,385 A | 11/1992 | Schumacher | |
| 5,178,768 A | 1/1993 | White, Jr. et al. | |
| 5,192,452 A | 3/1993 | Mitsui et al. | |
| 5,207,877 A | 5/1993 | Weinberg et al. | |
| 5,207,995 A | 5/1993 | Bosserman | |
| 5,213,779 A | 5/1993 | Kay et al. | |
| 5,227,168 A | 7/1993 | Chvapil et al. | |
| 5,236,595 A | 8/1993 | Wang et al. | |
| 5,238,488 A | 8/1993 | Wilhelm | |
| 5,248,398 A | 9/1993 | Cordani | |
| 5,251,716 A | 10/1993 | Pedersen et al. | |
| 5,356,437 A | 10/1993 | Shepperd et al. | |
| 5,260,066 A | 11/1993 | Wood et al. | |
| 5,281,253 A * | 1/1994 | Thompson | 95/22 |
| 5,326,737 A | 7/1994 | Kay et al. | |
| 5,328,669 A | 7/1994 | Han et al. | |
| 5,330,770 A | 7/1994 | Kuno | |
| 5,338,460 A | 8/1994 | Yen | |
| 5,344,479 A | 9/1994 | Kerfoot et al. | |
| 5,352,365 A | 10/1994 | Fuller | |
| 5,358,643 A | 10/1994 | Mcclintock | |
| 5,368,703 A | 11/1994 | Brewster | |
| 5,389,352 A | 2/1995 | Wang | |
| 5,403,495 A | 4/1995 | Kust et al. | |
| 5,409,522 A | 4/1995 | Durham et al. | |
| 5,422,489 A | 6/1995 | Bhargava | |
| 5,422,907 A | 6/1995 | Bhargava | |
| 5,433,931 A | 7/1995 | Bosserman | |
| 5,446,286 A | 8/1995 | Bhargava | |
| 5,455,489 A | 10/1995 | Bhargava | |
| 5,500,198 A | 3/1996 | Liu et al. | |
| 5,505,766 A | 4/1996 | Chang | |
| 5,529,811 A | 6/1996 | Sinko | |
| 5,543,126 A | 8/1996 | Ota et al. | |
| 5,545,604 A | 8/1996 | Demmel | |
| 5,551,976 A | 9/1996 | Allen | |
| 5,556,545 A | 9/1996 | Volcheck et al. | |
| 5,575,915 A | 11/1996 | Nakamura et al. | |
| 5,575,919 A | 11/1996 | Santina | |
| 5,580,535 A | 12/1996 | Hoke et al. | |
| 5,603,838 A | 2/1997 | Misra et al. | |
| 5,618,406 A | 4/1997 | Demmel | |
| 5,637,258 A | 6/1997 | Goldburt et al. | |
| 5,649,894 A | 7/1997 | White et al. | |
| 5,660,802 A | 8/1997 | Archer et al. | |
| 5,683,953 A | 11/1997 | Mills | |
| 5,688,378 A | 11/1997 | Khoe et al. | |
| 5,689,038 A | 11/1997 | Bartram et al. | |
| 5,698,212 A | 12/1997 | Hagiwara | |
| 5,702,592 A | 12/1997 | Suri et al. | |
| 5,707,508 A * | 1/1998 | Surma et al. | 205/688 |
| 5,711,930 A | 1/1998 | Albers et al. | |
| 5,712,218 A | 1/1998 | Chopin et al. | |
| 5,712,219 A | 1/1998 | Klabunde et al. | |
| 5,728,404 A | 3/1998 | Von Rheinbaben et al. | |
| 5,730,995 A | 3/1998 | Shirono et al. | |
| 5,759,855 A | 6/1998 | Pierschbacher et al. | |
| 5,759,939 A | 6/1998 | Klabunde et al. | |
| 5,783,057 A | 7/1998 | Tomita et al. | |
| 5,795,836 A | 8/1998 | Jin et al. | |
| 5,820,966 A | 10/1998 | Krause et al. | |
| 5,833,841 A | 11/1998 | Koslowsky | |
| 5,859,064 A | 1/1999 | Cronce | |
| 5,876,610 A | 3/1999 | Clack et al. | |
| 5,897,675 A | 4/1999 | Mangold et al. | |
| 5,897,781 A | 4/1999 | Dourdeville | |
| 5,897,784 A | 4/1999 | Mills | |
| 5,910,253 A | 6/1999 | Fuerstenau et al. | |
| 5,914,287 A | 6/1999 | Saito | |
| 5,914,436 A | 6/1999 | Klabunde et al. | |
| 5,918,555 A | 7/1999 | Winegar | |
| 5,922,926 A | 7/1999 | Back et al. | |
| 5,928,504 A | 7/1999 | Hembre et al. | |
| 5,938,837 A | 8/1999 | Hanawa et al. | |
| 5,939,087 A | 8/1999 | Hagiwara | |
| 5,952,665 A | 9/1999 | Bhargava | |
| 5,976,383 A | 11/1999 | Guess et al. | |
| 5,990,373 A | 11/1999 | Klabunde | |
| 5,994,260 A | 11/1999 | Bonneau | |
| 6,001,152 A | 12/1999 | Sinha | |
| 6,001,157 A | 12/1999 | Nogami | |
| 6,017,553 A | 1/2000 | Burrell et al. | |
| 6,030,537 A | 2/2000 | Shaniuk et al. | |
| 6,036,886 A | 3/2000 | Chhabra et al. | |
| 604,882 A | 4/2000 | Demmel et al. | |
| 6,045,925 A | 4/2000 | Klabunde et al. | |
| 6,057,488 A | 5/2000 | Koper et al. | |
| 6,087,294 A | 7/2000 | Klabunde et al. | |
| 6,093,236 A | 7/2000 | Klabunde et al. | |
| 6,093,325 A | 7/2000 | Stone | |
| 6,093,328 A | 7/2000 | Santina | |
| 6,099,819 A | 8/2000 | Srinivas et al. | |
| 6,114,038 A | 9/2000 | Castro et al. | |
| 6,123,323 A | 9/2000 | Yoneda et al. | |
| 6,132,623 A | 10/2000 | Nikolaidis et al. | |
| 6,136,749 A | 10/2000 | Gadkaree et al. | |
| 6,143,318 A | 11/2000 | Gilchrist et al. | |
| 6,146,539 A | 11/2000 | Mills | |
| 6,177,015 B1 | 1/2001 | Blakey et al. | |
| 6,180,016 B1 | 1/2001 | Johnston et al. | |
| 6,187,192 B1 | 2/2001 | Johnston et al. | |
| 6,187,205 B1 | 2/2001 | Martin et al. | |
| 6,197,201 B1 | 3/2001 | Misra et al. | |
| 6,197,204 B1 | 3/2001 | Heskett | |
| 6,200,482 B1 | 3/2001 | Winchester et al. | |
| 6,203,709 B1 | 3/2001 | Min et al. | |
| 6,214,238 B1 | 4/2001 | Gallup | |
| 6,221,118 B1 | 4/2001 | Yoshida et al. | |

| Patent | Kind | Date | Inventor |
|---|---|---|---|
| 6,221,602 | B1 | 4/2001 | Barbera-Guillem et al. |
| 6,221,903 | B1 | 4/2001 | Courchesne |
| 6,224,898 | B1 | 5/2001 | Balogh et al. |
| 6,238,566 | B1 | 5/2001 | Yoshida et al. |
| 6,238,686 | B1 | 5/2001 | Burrell et al. |
| 6,248,605 | B1 | 6/2001 | Harkonen et al. |
| 6,258,334 | B1 | 7/2001 | Gadkaree et al. |
| 6,264,841 | B1 | 7/2001 | Tudor |
| 6,294,006 | B1 | 9/2001 | Andou |
| 6,299,851 | B1 | 10/2001 | Li et al. |
| 6,300,640 | B1 | 10/2001 | Bhargava et al. |
| 631,910 | A1 | 11/2001 | Adefris et al. |
| 6,312,604 | B1 | 11/2001 | Denkewicz et al. |
| 6,326,326 | B1 | 12/2001 | Feng et al. |
| 6,328,779 | B1 | 12/2001 | He et al. |
| 6,338,800 | B1 | 1/2002 | Kulperger et al. |
| 6,341,567 | B1 | 1/2002 | Robertson et al. |
| 6,342,163 | B1 | 1/2002 | DeLonge et al. |
| 6,350,383 | B1 | 2/2002 | Douglas |
| 6,351,932 | B1 | 3/2002 | Hummel |
| 6,361,824 | B1 | 3/2002 | Yekimov et al. |
| 6,368,510 | B2 | 4/2002 | Friot |
| 6,372,003 | B1 | 4/2002 | Kasai et al. |
| 6,375,834 | B1 | 4/2002 | Guess et al. |
| 6,383,273 | B1 | 5/2002 | Kepner et al. |
| 6,383,395 | B1 | 5/2002 | Clarke et al. |
| 6,391,207 | B1 | 5/2002 | Cluyse |
| 6,391,869 | B1 | 5/2002 | Parks et al. |
| 6,395,659 | B2 | 5/2002 | Seto et al. |
| 6,395,736 | B1 | 5/2002 | Parks et al. |
| 6,403,653 | B1 | 6/2002 | Hobson et al. |
| 6,406,676 | B1 | 6/2002 | Sundkvist |
| 6,410,603 | B1 | 6/2002 | Hobson et al. |
| 642,043 | A1 | 7/2002 | Braue et al. |
| 6,417,423 | B1 | 7/2002 | Koper et al. |
| 6,428,705 | B1 | 8/2002 | Allen et al. |
| 6,440,300 | B1 | 8/2002 | Randall et al. |
| 6,444,143 | B2 | 9/2002 | Bawendi et al. |
| 6,452,184 | B1 | 9/2002 | Taskar et al. |
| 6,460,535 | B1 | 10/2002 | Nisewander et al. |
| 6,461,535 | B1 | 10/2002 | de Esparza |
| 6,468,499 | B1 | 10/2002 | Balachandran et al. |
| 6,475,451 | B1 | 11/2002 | Leppin et al. |
| 6,524,487 | B2 | 2/2003 | Kulperger et al. |
| 6,524,540 | B1 | 2/2003 | Heinig |
| 6,528,451 | B2 | 3/2003 | Brezny et al. |
| 6,536,672 | B1 | 3/2003 | Outwater |
| 6,537,382 | B1 | 3/2003 | Bartram et al. |
| 6,542,487 | B1 | 4/2003 | Ishii et al. |
| 6,542,540 | B1 | 4/2003 | Leung et al. |
| 6,551,514 | B1 | 4/2003 | Misra et al. |
| 6,562,092 | B1 | 5/2003 | Ito et al. |
| 6,562,403 | B2 | 5/2003 | Klabunde et al. |
| 6,569,224 | B2 | 5/2003 | Kerfoot et al. |
| 6,569,393 | B1 | 5/2003 | Hoke et al. |
| 6,569,490 | B2 | 5/2003 | Yadav et al. |
| 6,572,672 | B2 | 6/2003 | Yadav et al. |
| 6,576,092 | B2 | 6/2003 | Granite et al. |
| 6,576,156 | B1 | 6/2003 | Ratna et al. |
| 6,585,787 | B2 | 7/2003 | Yamasaki et al. |
| 6,589,496 | B1 | 7/2003 | Yabe et al. |
| 6,599,428 | B1 | 7/2003 | Douglas |
| 6,599,429 | B1 | 7/2003 | Azizian |
| 6,602,111 | B1 | 8/2003 | Fujie et al. |
| 6,602,671 | B1 | 8/2003 | Bawendi et al. |
| 6,610,264 | B1 | 8/2003 | Buchanan et al. |
| 661,323 | A1 | 9/2003 | Krulik et al. |
| 6,623,642 | B2 | 9/2003 | Robertson |
| 6,627,632 | B2 | 9/2003 | Parks et al. |
| 6,653,519 | B2 | 11/2003 | Koper et al. |
| 6,666,903 | B1 | 12/2003 | Green |
| 6,680,211 | B2 | 1/2004 | Barbera-Guillem et al. |
| 6,689,178 | B2 | 2/2004 | Ito et al. |
| 670,619 | A1 | 3/2004 | Jensen et al. |
| 6,706,082 | B2 | 3/2004 | Ota et al. |
| 6,716,895 | B1 | 4/2004 | Terry |
| 6,719,828 | B1 | 4/2004 | Lovell et al. |
| 6,723,349 | B1 * | 4/2004 | Hill et al. ............ 424/604 |
| 6,740,141 | B2 | 5/2004 | Espin et al. |
| 6,770,483 | B2 | 8/2004 | Lyon |
| 6,774,361 | B2 | 8/2004 | Bawendi et al. |
| 6,780,332 | B2 | 8/2004 | Shiau et al. |
| 6,790,363 | B2 | 9/2004 | Vempati |
| 6,790,420 | B2 | 9/2004 | Breen et al. |
| 6,790,521 | B1 | 9/2004 | Taketomi et al. |
| 6,800,204 | B2 | 10/2004 | Harck et al. |
| 6,808,692 | B2 | 10/2004 | Oehr |
| 6,821,414 | B1 | 11/2004 | Johnson et al. |
| 6,821,434 | B1 | 11/2004 | Moore et al. |
| 6,824,690 | B1 | 11/2004 | Zhao et al. |
| 6,827,766 | B2 | 12/2004 | Carnes et al. |
| 6,833,123 | B2 | 12/2004 | Huang et al. |
| 6,843,617 | B2 | 1/2005 | Chowdhury et al. |
| 6,843,919 | B2 | 1/2005 | Klabunde et al. |
| 6,843,923 | B2 | 1/2005 | Morton |
| 6,846,432 | B2 | 1/2005 | Mills |
| 6,849,187 | B2 | 2/2005 | Shaniuk |
| 6,852,903 | B1 | 2/2005 | Brown et al. |
| 6,855,665 | B1 | 2/2005 | Blake et al. |
| 6,858,147 | B2 | 2/2005 | Dukhin et al. |
| 6,860,924 | B2 | 3/2005 | Rajagopalan et al. |
| 6,861,002 | B2 | 3/2005 | Hughes |
| 6,862,825 | B1 | 3/2005 | Lowndes |
| 6,863,825 | B2 | 3/2005 | Witham et al. |
| 6,864,213 | B2 | 3/2005 | Labarge et al. |
| 6,881,424 | B1 | 4/2005 | Kemp et al. |
| 6,881,766 | B2 | 4/2005 | Hain |
| 6,883,825 | B2 | 4/2005 | Schneider |
| 6,887,302 | B2 | 5/2005 | Rajagopalan et al. |
| 6,887,566 | B1 | 5/2005 | Hung et al. |
| 6,896,809 | B2 | 5/2005 | Qian et al. |
| 6,901,684 | B2 | 6/2005 | Ito et al. |
| 6,905,527 | B2 | 6/2005 | Ito et al. |
| 6,905,698 | B1 | 6/2005 | Aldcroft et al. |
| 6,908,560 | B2 | 6/2005 | Guter |
| 6,908,570 | B2 | 6/2005 | Green |
| 6,908,628 | B2 | 6/2005 | Herruzo |
| 6,914,033 | B2 * | 7/2005 | Gislason et al. ............ 502/400 |
| 6,914,034 | B2 | 7/2005 | Vo |
| 6,919,029 | B2 | 7/2005 | Meng et al. |
| 6,921,739 | B2 | 7/2005 | Smith et al. |
| 6,927,501 | B2 | 8/2005 | Baarman et al. |
| 6,942,840 | B1 | 9/2005 | Broderick |
| 6,946,076 | B2 | 9/2005 | Mills |
| 6,946,578 | B2 | 9/2005 | Nakano et al. |
| 6,957,743 | B2 | 10/2005 | Johnston et al. |
| 6,960,329 | B2 | 11/2005 | Sellakumar |
| 6,974,564 | B2 | 12/2005 | Biermann et al. |
| 6,977,039 | B2 | 12/2005 | Knoll et al. |
| 6,986,798 | B2 | 1/2006 | Bessho et al. |
| 6,987,129 | B2 | 1/2006 | Mak et al. |
| 6,998,080 | B2 | 2/2006 | Stadermann et al. |
| 7,008,559 | B2 | 3/2006 | Chen |
| 7,014,782 | B2 | 3/2006 | D'Emidio et al. |
| 7,025,800 | B2 | 4/2006 | Campbell et al. |
| 7,029,516 | B2 * | 4/2006 | Campbell et al. ............ 95/90 |
| 7,033,419 | B1 | 4/2006 | Granite et al. |
| RE39,098 | E | 5/2006 | Klabunde et al. |
| 7,037,480 | B2 | 5/2006 | Bhinde |
| 7,048,853 | B2 | 5/2006 | Witham et al. |
| 7,048,860 | B2 | 5/2006 | Oishi |
| 7,049,382 | B2 | 5/2006 | Haftka et al. |
| 706,023 | A1 | 6/2006 | Srinivas et al. |
| 7,056,454 | B2 | 6/2006 | Fujino |
| 7,067,294 | B2 | 6/2006 | Singh et al. |
| 7,074,336 | B1 | 7/2006 | Teter et al. |
| 7,078,071 | B2 | 7/2006 | Taketomi et al. |
| 7,081,428 | B1 | 7/2006 | Thampi |
| 7,083,730 | B2 | 8/2006 | Davis |
| 7,094,383 | B2 | 8/2006 | Wang et al. |
| 7,101,415 | B2 | 9/2006 | Torres et al. |
| 7,101,493 | B2 | 9/2006 | Colucci |
| 7,112,237 | B2 | 9/2006 | Zeller et al. |
| 7,129,684 | B2 | 10/2006 | Park |
| 7,141,227 | B2 | 11/2006 | Chan |
| 7,156,888 | B2 | 1/2007 | Mochizuki |
| 7,156,994 | B1 | 1/2007 | Archer |
| 7,160,505 | B2 | 1/2007 | Belbachir et al. |

| | | | | | | |
|---|---|---|---|---|---|---|
| 7,179,849 B2 | 2/2007 | Terry | | 2004/0104377 A1 | 6/2004 | Phelps et al. |
| 7,183,235 B2 | 2/2007 | Lovell et al. | | 2004/0109853 A1 | 6/2004 | McDaniel |
| 7,186,671 B2 | 3/2007 | Smith et al. | | 2004/0202703 A1 | 10/2004 | Meyer-Ingold et al. |
| 7,192,602 B2 | 3/2007 | Fechner et al. | | 2004/0230086 A1 | 11/2004 | Okun et al. |
| 7,211,320 B1 | 5/2007 | Cooper et al. | | 2005/0008861 A1 | 1/2005 | Yadav et al. |
| 7,214,836 B2 | 5/2007 | Brown et al. | | 2005/0058689 A1 | 3/2005 | McDaniel |
| 7,241,629 B2 | 7/2007 | Dejneka et al. | | 2005/0067347 A1 | 3/2005 | Vanhulle et al. |
| 7,250,174 B2 | 7/2007 | Lee et al. | | 2005/0069464 A1 | 3/2005 | Obee et al. |
| 7,252,694 B2 | 8/2007 | Woo et al. | | 2005/0079415 A1 | 4/2005 | Boone et al. |
| 7,252,769 B2 | 8/2007 | Dickinson | | 2005/0084755 A1 | 4/2005 | Boone et al. |
| 7,256,049 B2 | 8/2007 | Bennett et al. | | 2005/0098503 A1 | 5/2005 | Kim |
| 7,276,640 B2 | 10/2007 | Mulukutla et al. | | 2005/0126338 A1 | 6/2005 | Yadav |
| 7,279,129 B2 | 10/2007 | Lanz et al. | | 2005/0126430 A1 | 6/2005 | Lightner, Jr. et al. |
| 7,282,153 B2 | 10/2007 | Barrett et al. | | 2005/0136486 A1 | 6/2005 | Haushalter |
| 7,291,272 B2 | 11/2007 | Bourke et al. | | 2005/0159307 A1 | 7/2005 | Okun et al. |
| 7,291,315 B2 | 11/2007 | Obee et al. | | 2005/0230659 A1 | 10/2005 | Hampden-Smith et al. |
| 7,297,263 B2 | 11/2007 | Nelson et al. | | 2005/0257724 A1 | 11/2005 | Guinther et al. |
| 7,297,656 B2 | 11/2007 | Zhang et al. | | 2005/0271941 A1 | 12/2005 | Bushong et al. |
| 7,300,587 B2 | 11/2007 | Smith et al. | | 2006/0000763 A1 | 1/2006 | Rinker et al. |
| 7,300,589 B2 | 11/2007 | Witham et al. | | 2006/0018954 A1 | 1/2006 | Kuttler |
| 7,310,898 B2 | 12/2007 | Wei et al. | | 2006/0030622 A1 | 2/2006 | Mak et al. |
| 7,329,356 B2 | 2/2008 | Brady | | 2006/0049091 A1 | 3/2006 | Cheetham et al. |
| 7,329,359 B2 * | 2/2008 | Roark ............... 210/763 | | 2006/0062831 A1 | 3/2006 | Meyer-Ingold et al. |
| 7,335,622 B2 | 2/2008 | Koyanaka et al. | | 2006/0070947 A1 | 4/2006 | Conrad |
| 7,335,808 B2 | 2/2008 | Koper et al. | | 2006/0120930 A1 | 6/2006 | Mizukami |
| 7,338,603 B1 | 3/2008 | McNew et al. | | 2006/0162260 A1 | 7/2006 | Nho et al. |
| 7,341,618 B2 | 3/2008 | Bayer et al. | | 2006/0178609 A1 | 8/2006 | Horn et al. |
| 7,341,667 B2 | 3/2008 | Kennard et al. | | 2006/0198883 A1 | 9/2006 | Parks et al. |
| 7,341,977 B2 | 3/2008 | Klabunde et al. | | 2006/0199301 A1 | 9/2006 | Basheer et al. |
| 7,361,279 B2 | 4/2008 | Hernandez | | 2006/0199733 A1 | 9/2006 | Grier et al. |
| 7,368,388 B2 | 5/2008 | Small et al. | | 2006/0224237 A1 | 10/2006 | Furst et al. |
| 7,368,412 B2 | 5/2008 | Tranter et al. | | 2006/0228275 A1 | 10/2006 | Rutman |
| 7,378,372 B2 * | 5/2008 | Sylvester ............... 502/416 | | 2006/0237369 A1 | 10/2006 | Kirts et al. |
| 7,422,759 B2 | 9/2008 | Kepner et al. | | 2006/0246149 A1 | 11/2006 | Buchholz et al. |
| 7,429,330 B2 | 9/2008 | Vo et al. | | 2006/0254930 A1 | 11/2006 | Martinie et al. |
| 7,431,758 B2 | 10/2008 | Ota et al. | | 2006/0257728 A1 | 11/2006 | Mortensen et al. |
| 7,438,828 B2 | 10/2008 | Young | | 2006/0275564 A1 | 12/2006 | Grah et al. |
| 7,445,718 B2 | 11/2008 | Misra et al. | | 2007/0000836 A1 | 1/2007 | Elefritz et al. |
| 7,459,086 B2 | 12/2008 | Gaid | | 2007/0012631 A1 | 1/2007 | Coffey et al. |
| 7,468,413 B2 | 12/2008 | Yokota et al. | | 2007/0017871 A1 | 1/2007 | Reddy et al. |
| 7,473,474 B2 | 1/2009 | Toreki et al. | | 2007/0080115 A1 | 4/2007 | Sylvester |
| 7,476,311 B2 | 1/2009 | Litz et al. | | 2007/0081931 A1 | 4/2007 | Cho et al. |
| 7,481,939 B2 | 1/2009 | Haley | | 2007/0114179 A1 | 5/2007 | Badger |
| 7,498,005 B2 | 3/2009 | Yadav | | 2007/0122327 A1 | 5/2007 | Yang et al. |
| 7,534,287 B2 | 5/2009 | Zeller et al. | | 2007/0128424 A1 | 6/2007 | Omori et al. |
| 7,534,453 B1 | 5/2009 | Rzigalinski et al. | | 2007/0134307 A1 | 6/2007 | Xiao et al. |
| 7,560,023 B2 | 7/2009 | Miyazawa et al. | | 2007/0142783 A1 | 6/2007 | Huey et al. |
| 7,566,393 B2 | 7/2009 | Klabunde et al. | | 2007/0149405 A1 | 6/2007 | Spitler et al. |
| 7,572,416 B2 | 8/2009 | Alward et al. | | 2007/0158251 A1 | 7/2007 | Chau |
| 7,588,744 B1 | 9/2009 | Sylvester | | 2007/0167971 A1 | 7/2007 | Huey et al. |
| 7,588,782 B2 | 9/2009 | Moerck et al. | | 2007/0169626 A1 | 7/2007 | Sullivan |
| 7,591,952 B2 | 9/2009 | Young | | 2007/0286796 A1 | 12/2007 | Koper et al. |
| 7,611,620 B2 | 11/2009 | Carson et al. | | 2007/0298085 A1 | 12/2007 | Lestage et al. |
| 7,645,540 B2 | 1/2010 | Boone et al. | | 2008/0050440 A1 | 2/2008 | Wakamura et al. |
| 7,661,483 B2 | 2/2010 | Mulukutla et al. | | 2008/0058206 A1 | 3/2008 | Misra et al. |
| 7,820,100 B2 | 10/2010 | Garfield et al. | | 2008/0058689 A1 | 3/2008 | Holloway et al. |
| 2001/0009831 A1 | 7/2001 | Schink et al. | | 2008/0081120 A1 | 4/2008 | Van Ooij et al. |
| 2001/0012856 A1 | 8/2001 | Parks et al. | | 2008/0090138 A1 | 4/2008 | Vu et al. |
| 2002/0003116 A1 | 1/2002 | Golden | | 2008/0093580 A1 | 4/2008 | Witham et al. |
| 2002/0005382 A1 | 1/2002 | Kulperger et al. | | 2008/0097271 A1 | 4/2008 | Lo et al. |
| 2002/0005383 A1 | 1/2002 | Voute et al. | | 2008/0102136 A1 | 5/2008 | Koper et al. |
| 2002/0044901 A1 | 4/2002 | Wildon et al. | | 2008/0156734 A1 | 7/2008 | Burba et al. |
| 2002/0066702 A1 | 6/2002 | Liu | | 2008/0199539 A1 | 8/2008 | Baker et al. |
| 2002/0072522 A1 | 6/2002 | Parks et al. | | 2008/0254146 A1 | 10/2008 | Huey et al. |
| 2002/0187990 A1 | 12/2002 | Parks et al. | | 2008/0254147 A1 | 10/2008 | Huey et al. |
| 2002/0198136 A1 | 12/2002 | Mak et al. | | 2008/0262285 A1 | 10/2008 | Black et al. |
| 2003/0015467 A1 | 1/2003 | Johnston et al. | | 2008/0264300 A1 | 10/2008 | Sato et al. |
| 2003/0133990 A1 | 7/2003 | Hursey et al. | | 2008/0302267 A1 | 12/2008 | Defalco |
| 2003/0149406 A1 | 8/2003 | Martineau et al. | | 2008/0311311 A1 | 12/2008 | Khan et al. |
| 2003/0156981 A1 | 8/2003 | Mills | | 2009/0001011 A1 | 1/2009 | Knipmeyer et al. |
| 2003/0180213 A1 | 9/2003 | Carnes et al. | | 2009/0011240 A1 | 1/2009 | Lenz et al. |
| 2003/0203977 A1 | 10/2003 | Klabunde et al. | | 2009/0011930 A1 | 1/2009 | Hagemeyer |
| 2003/0207949 A1 | 11/2003 | Klabunde et al. | | 2009/0012204 A1 | 1/2009 | Drechsler et al. |
| 2003/0215378 A1 | 11/2003 | Zhou et al. | | 2009/0069844 A1 | 3/2009 | Green et al. |
| 2004/0029715 A1 | 2/2004 | Schindler et al. | | 2009/0098016 A1 | 4/2009 | Koper et al. |
| 2004/0031764 A1 | 2/2004 | Heinig | | 2009/0101588 A1 | 4/2009 | Misra et al. |
| 2004/0043914 A1 | 3/2004 | Kaziska et al. | | 2009/0101837 A1 | 4/2009 | Kourtakis et al. |
| 2004/0050795 A1 | 3/2004 | Park et al. | | 2009/0107919 A1 | 4/2009 | Burba et al. |
| 2004/0091417 A1 | 5/2004 | Yadav | | 2009/0107925 A1 | 4/2009 | Burba et al. |

| | | | |
|---|---|---|---|
| 2009/0108777 A1 | 4/2009 | Hyde et al. | |
| 2009/0111289 A1 | 4/2009 | Vinther | |
| 2009/0111689 A1 | 4/2009 | Burba | |
| 2009/0120802 A1 | 5/2009 | Ciampi et al. | |
| 2009/0130169 A1 | 5/2009 | Bernstein | |
| 2009/0206042 A1 | 8/2009 | Landau et al. | |
| 2009/0264574 A1 | 10/2009 | Van Ooij et al. | |
| 2009/0299253 A1 | 12/2009 | Hursey | |
| 2010/0042206 A1 | 2/2010 | Yadav et al. | |
| 2010/0055456 A1 | 3/2010 | Perera et al. | |
| 2010/0243542 A1 | 9/2010 | Burba, III et al. | |
| 2010/0255559 A1 | 10/2010 | Burba, III et al. | |

FOREIGN PATENT DOCUMENTS

| | | |
|---|---|---|
| CN | 1248486 | 3/2000 |
| EP | 0191893 | 8/1986 |
| EP | 0541158 | 5/1993 |
| EP | 0597173 | 5/1994 |
| EP | 0812619 | 12/1997 |
| EP | 0939431 | 1/1999 |
| EP | 1201607 | 2/2002 |
| EP | 1080144 | 8/2002 |
| EP | 1452229 | 9/2004 |
| EP | 1071500 | 2/2005 |
| EP | 1870150 | 12/2007 |
| EP | 1992394 | 11/2008 |
| EP | 2161067 | 3/2010 |
| EP | 2177252 | 4/2010 |
| GB | 1447264 | 8/1976 |
| GB | 2426469 | 11/2006 |
| JP | 11/51917 | 6/1989 |
| JP | H2-17220 | 4/1990 |
| JP | 6-207561 | 7/1994 |
| JP | 10165948 | 6/1998 |
| JP | 11/090413 | 4/1999 |
| JP | 11/302684 | 11/1999 |
| JP | 11-302684 | 11/1999 |
| JP | 2000-024647 | 1/2000 |
| JP | 2000/024647 | 1/2000 |
| JP | 2002/205062 | 7/2002 |
| JP | 2002-282686 | 10/2002 |
| JP | 2002/349234 | 12/2002 |
| JP | 2004/050069 | 2/2004 |
| JP | 2004/057870 | 2/2004 |
| JP | 2004/305915 | 11/2004 |
| JP | 2004/330012 | 11/2004 |
| JP | 2005-023373 | 1/2005 |
| JP | 2005-028312 | 2/2005 |
| JP | 2005/028312 | 2/2005 |
| JP | 2005/048181 | 2/2005 |
| JP | 2005/288363 | 10/2005 |
| JP | 2005-288363 | 10/2005 |
| JP | 2006-320847 | 11/2006 |
| JP | 2006/320847 | 11/2006 |
| JP | 07/081932 | 3/2007 |
| JP | 07-081932 | 3/2007 |
| JP | 2010-083741 | 4/2010 |
| RU | 2136607 | 9/1999 |
| RU | 2178599 | 1/2002 |
| SU | 663291 | 5/1979 |
| SU | 1766848 | 10/1992 |
| WO | WO 95/11195 | 4/1995 |
| WO | WO 97/12672 | 4/1997 |
| WO | WO 98/07493 | 2/1998 |
| WO | WO 99/28239 | 6/1999 |
| WO | WO 00/24680 | 5/2000 |
| WO | WO 01/32799 | 5/2001 |
| WO | WO 01/32820 | 5/2001 |
| WO | WO 01/78506 | 10/2001 |
| WO | WO 03/092748 | 11/2003 |
| WO | WO 2004/076770 | 9/2004 |
| WO | 2004096433 A1 | 11/2004 |
| WO | WO 2005/028707 | 3/2005 |
| WO | WO 2005/042130 | 5/2005 |
| WO | WO 2005/056175 | 6/2005 |
| WO | WO 2005/075000 | 8/2005 |
| WO | WO 2005/081722 | 9/2005 |
| WO | WO 2006/011764 | 2/2006 |
| WO | WO 2006/044784 | 4/2006 |
| WO | WO 2006/047613 | 5/2006 |
| WO | WO 2006/070153 | 7/2006 |
| WO | WO 2006/102008 | 9/2006 |
| WO | WO 2006/117424 | 11/2006 |
| WO | WO 2007/011877 | 1/2007 |
| WO | WO 2007/041553 | 4/2007 |
| WO | WO 2007/120910 | 10/2007 |
| WO | WO 2008/151173 | 12/2008 |
| WO | WO 2009/064845 | 5/2009 |
| WO | WO 2009/142823 | 11/2009 |
| WO | WO 2010/010569 | 1/2010 |
| WO | WO 2010/010570 | 1/2010 |
| WO | WO 2010/010571 | 1/2010 |
| WO | WO 2010/010574 | 1/2010 |
| WO | WO 2010/019934 | 2/2010 |

OTHER PUBLICATIONS

Adschiri et al., "Hydrothermal Synthesis of Metal Oxide Fine Particles at Supercritical Conditions," Ind. Eng. Chem. Res. 2000, 39, 4901-4907.

Casey, "Mystery Ceramic could lead to cheaper, stronger hydrogen fuel cells," gas2.0, Oct. 12, 2009, available at http://gas2.org/2009/10/12/mystery-ceramic-could-lead-to-cheaper-stronger-solid-... 3 pages.

Paulenova et al., "Redox potentials and kinetics of the Ce3+/Ce4+ redox reaction and solubility of cerium sulfates in sulfuric acid solutions," Journal of Power Sources 109 (2002) 431-438.

Kozlova et al., "Overall water splitting over Pt/TiO2 catalyst with Ce3+/Ce4+ shuttle charge transfer system," International Journal of Hydrogen Energy 34 (2009) 138-146.

Kreh et al., "Selective Oxidations with Ceric Methanesulfonate and Ceric Trifluoromethanesulfonate" Tetrahedron Letters, vol. 28, No. 10, pp. 1067-1068, 1987.

Lemont et al., "Promising optimization of the CeO2/CeCl3 cycle by reductive dissolution of cerium(IV) oxide," International Journal of Hydrogen Energy 33 (2008) 7355-7360.

Romero et al., "Syntheses, Crystal Structures, and Characterization of Bismuth Phosphates," Inorg. Chem. 1994, 33, 1869-1874.

Singh et al., "Ce0.67Cr0.33O2.11: A New Low-Temperature O2 Evolution Material and H2 Generation Catalyst by Thermochemical Splitting of Water†" Chem. Matter. 2009, 7 pages.

Viricelle et al., "Transformation of cerium(III) hydroxycarbonate into ceria. Part 1—Nucleation and growth rates of ceria," J. Chem. Soc., Faraday Trans., 1995, 91, 4431-4435.

Zhang, Y., Yang, M., and Huang, X., Arsenic(V) removal with a Ce(IV)-doped iron oxide adsorbent, Chemosphere 51 (2003) 945-952.

U.S. Appl. No. 11/958,602, filed Dec. 18, 2007, Burba et al.
U.S. Appl. No. 11/958,644, filed Dec. 18, 2007, Burba et al.
U.S. Appl. No. 11/958,968, filed Dec. 18, 2007, Burba et al.

"Bastnasite", available at htt://webmineral.com/data/Bastnasite-(Ce).shtml, accessed Jul. 30, 2007, 6 pages.

"Carbonates", available on the Molycorp website Dec. 13, 2005, pp. 22-30.

"Cerium: A Guide to its role in Chemical Technology", Molycorp, 1992, 48 pages.

"Clear Choices for Clean Drinking Water", Consumer Reports Jan. 2003, pp. 33-37.

"Foul Release System and Drag", Proceedins of the PCE 2001 Conference, pp. 273-286, Antwerp, 12 pages.

"Homogeneous Reactions of As and Se Oxoanions in Aqueous Solutions, and the Photooxidation of their Reduced Species in the X-ray Beam", available at http://geoweb.princeton.edu/research/geochemistry/research/aqueous-oxoanion.html, accessed May 6, 2009.

"Hydrometallurgy", Hazen Research, INC., available at http://www.hazenusa.com/hydrometallurgy-1.php, accessed Dec. 21, 2006, 7 pages.

"Potentiometry", date unknown, 14 pages.

"The Bacteriostatic Activity of Cerium, Lanthanum, and Thallium", Burkes et al., Journal of Bateriology, 54:417-24 (1947).

"UI Arsenic water treatment project shows promise", University of Idaho, Environmental News Network, Dec. 3, 2002, 2 pages.

Ahmed et al., "Arsenic Mitigation in Bangladesh", Oct. 2002, 67 pages.
Ahmed et al., "Arsenic Mitigation Technologies in South and East Asia", 44 pages, date unknown.
Ahmed, "Water Supply Options", available at http://www.physics.harvard.edu/~wilson/arsenic/conferences/Feroze_Ahmed/Sec_3..., accessed May 8, 2009, 25 pages, Jan. 29, 2002.
Ahmed, M. Feroze, "An Overview of Arsenic Removal Technologies in Bangladesh and India," Buet-Unu International Workshop on Technologies for Arsenic Removal from Drinking Water, May 5-7, 2001, pp. 251-269.
Ali et al., "Fate of Arsenic in Wastes Generated from Arsenic Removal Units", Bangladesh University of Engineering and Technology, date unknown, pp. 147-159.
Amimono, "Arsenic removal by inorganic ion-exchanger", available at http://www.apec-vc.or.jp/e/modules/tinyd00/index.php?id=63&kh_open_cid_00=7, accessed May 8, 2009.
Arsenate, Wikipedia, available at http://en.wikipedia.org/w/index.php?title=Arsenate&printable=yes, accessed May 6, 2009, 2 pages.
Banu et al., "Fabrication of Diffraction-encoded micro-particles using nano-imprint lithography", J. Micromech. Microeng. 17 (2007) S116-S121.
Chambers et al., "Modern approaches to marine antifouling coatings", Surface & Coatings Technology 201 (2006) 3642-3652.
Chi et al., "Preparation of Enriched Cerium Oxide from Bastnasite with Hydrochloric Acid by Two-Step Leaching", Metallurgical and Materials Transactions B, vol. 37B, Apr. 2006-155.
ClearWater Filtration Systems, Press Release, "New Filtration Patent to Revolutionize Home Water Filtration: Arsenic Levels Can Now be Controlled".
Clifford et al., "Oxidizing Arsenic III to Arsenic V for Better Removal", Water & Wastes Digest, Water Quality Products, Mar. 2001, vol. 6, No. 3, available at http://www.wwdmag.com/Oxidizing-Arsenic-III-to-Arsenic-V-for-Better-Removal-..., accessed May 6, 2009, 2 pages.
Corvini et al., "Mercury Removal from Natural Gas and Liquid Streams", UOP LLC, 11 pages, date unknown.
Dejneka et al., "Rare earth-doped glass microbarcodes", PNAS, Jan. 21, 2003, vol. 100, No. 2, 389-393.
Emsley, "The Elements" Third Edition, 1998, pp. 22-23, 26-27, 54-55, 110-111.
Everett et al., "Study of the Uncatalyzed Oxidation of Arsenic(III) by Cerium(IV) in Perchloric Acid Medium", Jan. 10, 1971, Stanford University.
Fujikawa et al., "Simulteneous removal of arsenic, iron and manganese in biological treatment unit", available at http://www.apec-vc.or.jp/e/modules/tinyd00/index.php?id=65&kh_open_cid_00=7, accessed May 8, 2009, 3 pages.
Fujikawa et al., "The aim of this special edition", Kyoto University, available at http://www.apec-vc.or.jp/e/modules/tinyd00/index.php?id=61&kh_open_cid_00=7, accessed May 8, 2009.
Goldberg, "Competitive Adsorption of Arsenate and Arsenite on Oxides and Clay Minerals", Soil Sci. Soc. Am. J. 66:413-421 (2002).
Gordon, "Network Progress: an Update from the Secretariat", World Health Organization: International Network to Promote Household Water Treatment and Safe Storage, Issue 2, May 2005, 10 pages.
Granite et al., "Novel Sorbents for Mercury Removal from Flue Gas", Ind. Eng. Chem. Res. 2000, 39, 1020-1029.
Granite et al., "Sorbents for Mercury Capture from Fuel Gas with Application to Gasification Systems", Ind. Eng. Chem. Res. 2006, 45, 4844-4848.
Granite et al., "Techniques for Mercury Control and Measurement in Gasification Systems", Presented at the 5th International Symposium on Gas Cleaning at High Temperature, Morgantown, WV, Sep. 2002, pp. 1-5.
Harck, "Arsenic in the US", Clean Water Filtration Systems, Jan. 2002, 42 pages.
Harper et al., "Removal of arsenic from wastewater using chemical precipitation methods", Water Environment Research, vol. 64, No. 3, 200-203.
Hayes et al., "The Phase Stability of Cerium Species in Aqueous Systems", Journal of the Electrochemical Society, 149 (12) C623-C630 (2002).

Hemmila et al., "Progree in Lanthanides as Luminscent Probes", Journal of Fluorescence, vol. 15, No. 4, Jul. 2005, 529-542.
Housecroft et al., "Inorganic Chemistry", 2001, Pearson Prentice Hall, chapter 7, pp. 170-186; chapter 14, pp. 338-344; Appendix 11, pp. 752-754; chapter 24, pp. 622-640.
Jadhav, "Development and Evaluation of Nanoscale Sorbents for Mercury Capture from Warm Fuel Gas", Aug. 25, 2006, 44 pages.
Johnston et al., "Safe Water Technology for Arsenic Removal", Technologies for Arsenic Removal from Drinking Water, pp. 1-22, date unknown.
Jones et al., "Arsenic 2000: An Overview of the Arsenic Issue in Bangladesh", Water Aid Bangladesh, Dec. 2000, pp. 1-70.
Kahakachchi et al., "Extraction of arsenic species from spiked soils and standard reference materials", Analyst 2004, 129, 714-718.
Kim et al., "Carbonate Effects in the Electrochemical Oxidation of Arsenite", Electrochemical Methods for Wastewater and Potable Water Treatment, Preprints of Extended Abstracts, vol. 42, No. 2, 2002.
Lambert, Human Health and Toxicology Information Sheet for Lanthanum Concentrate (5210/5212) and Lanthanum Lantanum Chloride (5240/5241), pp. 1-8, University of California, Irvine.
Link et al., "Inorganic Nanoparticles for Transfection of Mammalian Cells and Removal of Viruses from Aqueous Solutions", Biotechnology and Bioengineering, vol. 98, No. 5, Dec. 1, 2007, 1083-1093.
Lipps et al., "Arsenic Removal from Drinking Water by Adsorptive Media", U.S. EPA Demonstration Project at Spring Brook Mobile Home Park in Wales, ME, Six-Month Evaluation Report, Sep. 2006, 12 pages.
M. Jang et al., "Remediation of Arsenic-Contaminated Solids and Washing Effluents", Chemosphere, 60, pp. 344-354, (2005).
M.G.M. Alam et al., "Chemical Extraction of Arsenic from Contaminated Soil", J. Environ Sci Health A Tox Hazard Subst Environ Eng., 41 (4), pp. 631-643 (2006 ).
M.G.M. Alam et al., "Extraction of arsenic in a synthetic arsenic-contaminated soil using phosphate", Chemosphere 43 (2001) 1035-1041.
Murcott et al., "Innovative and Sustainable Technologies to Address the Global Arsenic Crisis", Sandia National Laboratories 2005 Vendor's Forum, Albuquerque, New Mexico, Nov. 2, 2005, 85 pages.
Mushak, "Potential Impact of Acid Precipitation on Arsenic and Selenium", Environmental Health Perspectives vol. 65, pp. 105-113, 1985.
Ohashi, "Arsenic removal technology—Arsenic removal using manganese oxide", available at http://www.apec-vc.or.jp/e/modules/tinyd00/index.php?id=64&kh_open_cid_00=7, accessed May 8, 2009, 5 pages.
Puraspec 1156 Mercury Removal, Johnson Matthey Catalysts 2003, 2 pages.
Puszynski et al., "Demonstration Project for Arsenic Removal from Drinking Water at Keystone, South Dakota", Mar. 15, 2005, 23 pages.
S.R. Al-Abed et al., "Arsenic Release from Iron Rich Mineral Processing Waste; Influence of pH and Redox Potential", Chemosphere, 66, pp. 775-782 (2007).
Shimoto, "Arsenic Removal Technology—Cerium adsorbent", available at http://www.apec-vc.or.jp/e/modules/tinyd00/index.php?id=62&kh_open_cid_00=7, accessed May 8, 2009, 4 pages.
Smith et al., "American Rare Earth Minerals: The Indispensable Resource for Clean Energy Technologies", Molycorp Minerals, LLC, Prepared for Congressional Leaders Jan. 29, 2009, 21 pages.
Stiltner, "Mercury Removal from Natural Gas and Liquid Streams", 2001, UOP LLC, 10 pages.
Tannehill, "Naturally Occurring Arsenic and Mercury" Proceedings from the Seventy-Fifth Gas Processors Association Conference, May 2007, pp. 54-55.
Thill et al., "Cytotoxicity of CeO2 Nanoparticles for *Escherichia coli*. Physico-Chemical Insight of the Cytotoxicity Mechanism", Environ. Sci. Technol. 2006, 40, 6151-6156.
Tributyltin, available at http://pmep.cce.cornell.edu/profiles/extoxnet/pyrethrins-ziram/tributyltin-ext.html, accessed Jul. 3, 2008, 6 pages.
Vu et al., "Review of Arsenic Removal Technologies for Contaminated Groundwaters", Argonne National Laboratory, Apr. 2003, 41 pages.

Wasay et al., "Adsorption of fluoride, phosphate, and arsenate ions on lanthanum-impregnated silica gel", Water Environment Research, vol. 68, No. 3 (May-Jun. 1996), pp. 295-300.
Yates et al., "Kinetics of the Iodide-catalyzed Reaction between Cerium(IV) and Arsenic(III)", Jan. 19, 1956, Yale University.
Yotsumoto et al., "Latest functions and introduction cost of water treatment technique, Water treatment technique using cerium based adsorbent and examples", Plant and Process, vol. 47, No. 8, pp. 60-63 (2005), Japan.
Yu et al., "The Phase Stability of Cerium Species in Aqueous Systems", Journal of the Electrochemical Society, 153 (1) C74-C79 (2006).
Zhang et al., "Arsenate adsorption on an Fe-Ce bimetal oxide adsorbent : Role of surface properties", Jan. 1, 2005,Institute of Research and Innovation, Japan.
Zhou et al., "Cryptography based on the absorption/emission features of multicolor semiconductor nanocrystal quantum dots", Optics Express, Jun. 28, 2004, vol. 12, No. 13, 2925-2931.
International Search Report for International Application No. PCT/US08/81084, mailed Dec. 23, 2008.
Written Opinion for International Application No. PCT/US09/81084, mailed Dec. 23, 2008.
Baker et al., "Present General Status of Understanding of Heteropoly Electrolytes and a Tracing of Some Major Highlights in the History of Their Elucidation", Chem. Rev., 1998, vol. 98, No. 1, pp. 3-50.
Chang, et al., "Wet air oxidation of a reactive dye solution using CoAlPO4-5 and CeO2 catalysts", Chemosphere, Aug. 2003, vol. 52, No. 6, pp. 943-949.
Coronado et al., "Polyoxometalate-based Molecular Materials", Chem. Re., 1998, vol. 98, No. 1, pp. 273-296.
Fertonani et al., "Solid State Reactions of Mercury with Pure Noble Metals Part 2 Mercury iridium system", Journal of Thermal Analysis and Calorimetry, 2002, vol. 67, pp. 403-409.
Gouzerh et al., "Main-Group Element, Organic, and Organometallic Derivatives of Polyoxometalates", Chem. Re., 1998, vol. 98, No. 1, pp. 77-112.
Hakuta et al., "Production of Ultra-fine Ceria Particles by Hydrothermal Synthesis Under Supercritical Conditions", Journal of Materials Science Letters, 1998, vol. 17, pp. 1211-1213.
Haron et al., "Sorption removal of arsenic by cerium-exchanged zeolite P", Materials Science and Engineering B, 2008, vol. 149, pp. 204-208.
Henderson, et al., "Redox properties of water on the oxidized and reduced surfaces of CeO2(111)", Surface Science, Feb. 20, 2003, vol. 526, Nos. 1-2, pp. 1-18, Environ. Molecular Sci. Lab., Pacific Northwest Nat. Lab., Richland, WA.
Hill, "Introduction: Polyoxometalates—Multicomponent Molecular Vehicles to Probe Fundamental Issues and Practical Problems", Chem. Re., 1998, vol. 98, No. 1, pp. 1-2.
Jeannin, "The Nomenclature of Polyoxometalates: How to Connect a Name and a Structure", Chem. Rev., 1998, vol. 98, No. 1, pp. 51-76.
Katsoulis, "A Survey of Applications of Polyoxometalates," Chem. Re., 1998, vol. 98, No. 1, pp. 359-388.
Klemperer et al., "Polyocoanion Chemistry Moves toward the Future: From Solids and Solutions to Surfaces," Chem. Re., 1998, vol. 98, No. 1, pp. 297-306.
Kozhevnikov, "Catalysis by Heteropoly Acids and Multicomponent Polyoxometalates in Liquid-Phase Reactions", Chem. Re., 1998, vol. 98, No. 1, pp. 171-198.
Lin, et al."Catalytic wet air oxidation of phenol by various CeO2 catalysts", Water Research, 2002, vol. 36, pp. 3009-3014.
Liu, et al. "Effect of CeO2 doping on catalytic activity of Fe2O3/gamma-Al2O(3) catalyst for catalytic wet peroxide oxidation of azo dyes", J. Hazard. Mater., May 8, 2007, vol. 143, Nos. 1-2, pp. 448-454, School of Municipal & Environmental Engineering, Harbin Institute of Technology, China.
Lopez-Anton, et al., "Retention of mercury in activated carbons in coal combustion and gasification flue gases", Fuel Processing Technology, Jun. 20, 2002, vol. 77-78, pp. 353-358.
Lowell et al., "Selection of Metal Oxides for Removing SO2 From Flue Gas", Ind. Eng. Chem. Proc. Des. Dev., 1971, vol. 10, No. 3, pp. 384-390.

Mizuno et al., "Heterogeneous Catalysis", Chem. Re., 1998, vol. 98, No. 1, pp. 199-218.
Muller et al., "Polyoxometalates: Very Large Clusters—Nanoscale Magnets", Chem. Re., 1998, vol. 98, No. 1, pp. 239-272.
Oztekin, "Recovery of Acides from Salt Forms", Desalinatio, 2007, vol. 212, pp. 62-69.
Peng et al., "Ceria nanoparticles supported on carbon nanotubes for the removal of arsenate from water", Materials Letters, 2005, vol. 59, pp. 399-403.
Portzer et al., "Development of novel sorbents for mercury control at elevated temperatures in coal-derived syngas: Results of initial screening of candidate materials", Fuel Process. Technol. 2004, vol. 85 pp. 621-630.
Rhule et al., "Polyoxometalates in Medicine," Chem. Re., 1998, vol. 98, No. 1, pp. 327-358.
Sadakane et al., "Electrochemical Properties of Polyoxometalates as Electrocatalysts", Chem. Re., 1998, vol. 98, No. 1, pp. 219-238.
Seida, et al., "Synthesis of clay-cerium hydroxide conjugates for the adsorption of Arsenic", Adsorption Science and Technology, Dec. 2005, vol. 23, No. 8, pp. 607-618.
Song, et al., "Mechanism of the Photocatalytic Degradation of C.I. Reactive Black 5 at pH 12.0 Using SrTiO3/CeO2 as the Catalyst", Environmental Science & Technology, 2007, vol. 41, No. 16, pp. 5846-5853, College of Biological and Environmental Engineering, China.
Song, et al., "Photocatalytic degradation of C.I. Direct Red 23 in aqueous solutions under UV irradiation using SrTiO3/CeO2 composite as the catalyst", Journal of Hazardous Materials, Apr. 15, 2008, vol. 152, No. 3, pp. 1301-1308, College of Biological and Environmental Engineering, China.
Spiro et al., J. Chem. Soc. 1965, 78-96.
Spotnitz, et al., "Mediated electrosynthesis with cerium (IV) in methanesulphonic acid", Journal of Applied Chemistry, Mar. 1990, vol. 20, No. 2, 209-215.
Trovarelli, "Cerium Dioxide : a key component in environmental catalysis", RICH MAC Magazine, La Chimica e L'Industria, Sep. 1996, vol. 78, pp. 823-829.
Weinstock, "Homogeneous-Phase Electron-Transfer Reactions of Polyoxometalates", Chem. Re., 1998, vol. 98, No. 1, pp. 113-170.
Worthington et al., "Kinetics and Analytical Applications of the Ruthenium Catalyzed Reaction between Cerium(IV) and Arsenic(II1) in Sulferic Acid Medium", Analytical Chemistry, Sep. 1970, vol. 42, No. 11, pp. 1157-1164, Purdue University.
Yamase, "Photo- and Electrochromism of Polyoxometalates and Related Materials," Chem. Re., 1998, vol. 98, No. 1, pp. 307-326.
Examination Report for Bangladesh Application No. 285/2008, dated Mar. 13, 2009.
Yang et al., "Decontamination of Chemical Warfare Agents", Chem Rev., 1992, vol. 92, pp. 1729-1743.
Notice of Allowance for Bangladesh Patent Application No. 225/2009, dated Nov. 22, 2009.
U.S. Appl. No. 12/721,233, filed Mar. 10, 2010, Burba et al.
U.S. Appl. No. 12/725,114, filed Mar. 16, 2010, Whitehead et al.
U.S. Appl. No. 12/757,788, filed Apr. 9, 2010, Whitehead et al.
"NanoActive Cerium Oxide," NanoScale Corporation, NA106.v.3 Apr. 1, 2008, 2 pages.
"NanoActive Granules," NanoScale Corporation, available at http://www.nanoscalecorp.com/content.php/chemicals/granules/, printed Apr. 2, 2010, 2 pages.
"NanoActive Metal Oxides," NanoScale Corporation, available at http://www.nanoscalecorp.com/content.php/chemicals/home/, printed Apr. 2, 2010, 2 pages.
"NanoActive Powders," NanoScale Corporation, available at http://www.nanoscalecorp.com/content.php/chemicals/powders/, printed Apr. 2, 2010, 2 pages.
"NanoActive Suspensions," NanoScale Corporation, available at http://www.nanoscalecorp.com/content.php/chemicals/suspensions/, printed Apr. 2, 2010, 2 pages.
Australian Drinking Water Guidelines, H2O: Part V Facts Sheets, date unknown, 355 pages.
Cartwright, P.S., "A Residential Drinking Water Treatment Primer: Part 1," Water Conditioning and Purification, Feb. 2008, 6 pages.

Klabunde, K., "Overview of NanoScale: Its Technology and Capabilities," slideshow presentation by NanoScale, date unknown, 31 pages.

Pradeep, T., "Affordable clean water using nanotechnology," Indian Institute of Technology Madras, Potential Environmental Benefits of Nanotechnology: Fostering safe innovation-led growth, OECD Jul. 15-17, 2009, 58 pages.

Williams et al., "Drinking water: New disinfecting medium boosts water treatment," Filtration+Separation, Mar./Apr. 2010, pp. 16-19.

Youngran, J. et al., "Effect of competing solutes on arsenic (V) adsorption using iron and aluminum oxides," Journal of Environmental Sciences, vol. 19(8), 2007, pp. 910-919 (Abstract Only).

International Preliminary Report on Patentability for International Application No. PCT/US09/81084, mailed May 14, 2010.

Background of the Invention for the above-captioned invention filed Oct. 31, 2007 (previously provided).

Cotton, "Modern inorganic chemistry," part 2, Moscow, World, 1969, pp. 202-203.

Sukharev, "Synthesis and use of specific oxyhydrate sorbents," Moscow, Energoatomizdat, 1987, pp. 75-102.

Firsching, "Solubility Products of the Trivalent Rare-Earth Arsenates," J. Chem. Eng. Data, 1992, vol. 37, pp. 497-499.

Firsching et al., "Solubility Products of the Trivalent Rare-Earth Phosphates," J. Chem. Eng. Data, 1991, vol. 36, pp. 93-95.

Jiang et al., "Biological nano-mineralization of Ce phosphate by *Saccharomyces cerevisiae*," Article in Press, Chemical Geology, 2010, vol. xxx, pp. xxx-xxx, 9 pages.

Nilchi et al., "Adsorption of selected ions on hydrous cerium oxide," Journal of Radioanalytical and Nuclear Chemistry, 2009, vol. 279(1), pp. 65-74.

Ho et al., "Removal of fluoride from water through ion exchange by mesoporous Ti oxohydroxide," Journal of Colloid and Interface Science, 2004, vol. 272, pp. 399-403.

Ishihara et al., "Pore size control for mesoporous titanium hydroxide prepared with mixed template molecules and its fluoride ion-exchange property," Microporous and Mesoporous Materials, 2009, vol. 122, pp. 87-92.

Official Action (English translation only) for Russian Patent Application No. 2008107341, dated Jun. 2, 2010.

U.S. Appl. No. 12/814,049, filed Jun. 11, 2010, Burba III et al.

U.S. Appl. No. 12/831,054, filed Jul. 6, 2010, Hassler et al.

U.S. Appl. No. 12/942,847, filed Nov. 9, 2010, Lupo et al.

"Distinguishing Adsorption and Surface Precipitation of Phosphate and Arsenate on Hydrous Iron Oxides," http://www.eng.nus.edu.sg/EResnews/0206/rd/rd_1.html, accessed Jul. 25, 2010, 4 pages.

Creaser et al., "X-ray photoelectron spectroscopic study of the oxidation and reduction of a cerium(III) oxide/cerium foil substrate," Catalysis Letters, 1994, vol. 23, pp. 13-24.

Heckert et al., "The role of cerium redox state in the SOD mimetic activity of nanoceria," Biomaterials, Jun. 2008, vol. 29, pp. 2705-2709.

Higuchi et al., "Electronic structure of protonic conductor $SrCeO_3$ by soft-X-ray spectroscopy," Solid State Ionics, Nov. 2004, vol. 175, pp. 549-552.

Li et al., "Synergism between rare earth cerium(IV) ion and vanillin on the corrosion of steel in $H_2SO_4$ solution: Weight loss, electrochemical, UV-vis, FTIR, XPS, and AFM approaches," Applied Surface Science, Jun. 2008, vol. 254, pp. 5574-5586.

Mullins et al., "Electron spectroscopy of single crystal and polycrystalline cerium oxide surfaces," Surface Science, Jul. 1998, vol. 409, pp. 307-319.

Raichur et al., "Adsorption of fluoride onto mixed rare earth oxides," Separation and Purification Technology, 2001, vol. 24, pp. 121-127.

Romeo et al., "XPS Study of the Reduction of Cerium Dioxide," Surface and Interface Analysis, May 1993, vol. 20, pp. 508-512.

Sharmin, "Arsenic Removal Processes on Trial in Bangladesh," Technologies for Arsenic Removal from Drinking Water, BUET-UNU International Workshop, Dhaka, Bangladesh, May 5-7, 2001, pp. 23-30.

Tahir, Muhammad Aslam, "Project-3: Innovative Low Cost Arsenic Removal Technologies," Thesis entitled Assessment of Arsenic and other Health Significant Water Quality Parameters in Ground Water of Northern Punjab, Department of Chemistry/ Bahauddin Zakariya University Multan, 2004, pp. 92-134.

Wakita et al., "A Synthetic Study of the Solid Solutions in the Systems $La_2(CO_3)_3 \cdot 8H_2O-CE_2(CO_3) \cdot H_2O$ and $La(OH)CO_3$-$CE(OH)CO_3$," Bulletin of the Chemical Society of Japan, 1979, vol. 52(2), pp. 428-432.

Youngran, J. et al., "Effect of competing solutes on arsenic (V) adsorption using iron and aluminum oxides," Journal of Environmental Sciences, vol. 19(8), 2007, pp. 910-919.

Yuliati et al., "Ce L[sub]III-edge Xanes Study on Valence of alumina-supported cerium oxide," Photon Factory Activity Report 2004 #22 Part B, User's Report, 2005, pp. 56.

U.S. Appl. No. 13/010,609, filed Jan. 20, 2011, Burba.

Dos Santos et al., "Review paper on current technologies for decolourisation of textile wastewaters: Perspectives for Anaerobic biotechnology," Bioresource Technology, 2007, vol. 98, pp. 2369-2385.

Gupta et al., "Novel Fluoropolymer-Based Striving for," www.PCIMAG.COM, Jul. 2007, pp. 70-80.

Kirk-Othmer, ed., "Colorants for Foods, Drugs, Cosmetics, and Medical Devices," Encyclopedia of Chemical Technology, Fourth Edition, vol. 6, 1998, John Wiley & Sons, pp. 892-941.

Kirk-Othmer, ed., "Dye Carriers," Encyclopedia of Chemical Technology, Fourth Edition, vol. 8, 1998, John Wiley & Sons, pp. 533-600.

"APV Engineered Coatings Kynar®," Presentation by APV Engineered Coatings, http://www.apvcoatings.com/cms/resource_library/files/8537e627f567af63/kynar_presentation_weiss_inc_fiber_board_cement_pdf_.pdf, date unknown, 30 pages.

"Benchtop Granulator™," LCI Corporation Technical Bulletin TB-GR-101, 2004, http://replay.waybackmachine.org/20040518160414/http://www.lcicorp.com/granulation/Docs/benchtop_tb.pdf, 1 page.

"New Products Kynar Aquatec from Arkema Inc.," metalmag Magazine, posted May 28, 2009, 2 pages.

"PolyGoneLines," Schaner's Waste Water Products, Inc., available at http://www.struvite.com/products.html#polygone_lines, date unknown, 3 pages.

"Radial Xtruder® Model EXDCS-60," LCI Corporation Technical Bulletin, 2006, http://replay.waybackmachine.org/20060511144227/http://www.lcicorp.com/granulation/Docs/xtruder60G_%20tb.pdf, 2 pages.

"Twin Dome Extruder Model TDG-80G," LCI Corporation Technical Bulletin, 2006, http://replay.waybackmachine.org/20060511145629/http://www.lcicorp.com/granulation/Docs/tdg80_extruder_%20tb.pdf, 2 pages.

"Virus," Wikipedia the free encyclopedia, http://wn.wikipedia.org/w/index.php?title=Virus&printable=yes, last modified Mar. 16, 2009, 28 pages.

Kirk et al., "Pigments," Kirk-Othmer Encyclopedia of Chemical Technology, Fourth Edition, vol. 19, 1996, John Wiley & Sons, pp. 1-77.

Kroschwitz et al., eds., "Lanthanides," Kirk-Othmer Encyclopedia of Chemical Technology, Fourth Edition, vol. 14, 1995, John Wiley & Sons, pp. 1091-1115.

Press Release, "Arkema proudly announces a new water-based fluoropolymer platform: Kynar® Aquatec™," Arkema Inc., Jun. 26, 2006, available at http://www.arkemasalescorner.com/kynar.page.cfm?pag=985&PRR_ID=669, 1 page.

Press Release, "Kynar Aquatec® FMA Resins: Cool-Roof Coatings are Now Significantly Longer Lasting," Arkema Inc., Aug. 24, 2009, available at http://www.arkema-inc.com/index.cfm?pag-343&PRR, 1 page.

Qureshi et al., "Synthesis, Dehydration Studies, and Cation-Exchange Behavior of a New Phase of Niobium(V) Phosphate," Bull. Chem. Soc. Jpn., Oct. 1986, vol. 59, pp. 3247-3255.

Surasitani et al., "Kinetics of the Ruthenium-Catalyzed Arsenic (111)-Cerium(IV) Reaction," J. Phys. Chem., 1959, vol. 63(6), pp. 890-892.

Tu, C., "A Study of Availability of Soil Arsenic (in Chinese)" Journal of Southwest Agricultural University, Dec. 1992, vol. 14 (6), pp. 447 (includes English translation).

Yong et al., "Nitrogen and Phosphorous Removal in Municipal Wastewater Treatment Plants in China: A Review," International Journal of Chemical Engineering, accepted Apr. 26, 2010, 10 pages.
Filtronics "NXT-2 Adsorptive media for arsenic removal," at http://www.filtronics.com/nxt2.htm, date unknown, copyright 1998, 2008, 2 pages.
Dauber, "Anaerobtechnik. Handbuch der anaeroben Behandlung von Abwasser und Schlamm," 1993, pp. 340-341 (includes translation).
Primer for Municipal Wastewater Treatment Systems, U.S. Environmental Protection Agency, EP 832-R-04-001, Sep. 2004, pp. 1-29.
Municipal Wastewater Treatment Plant Energy Baseline Study, PG&E New Construction Energy management Program, prepared by M/J Industrial Solutions, San Francisco, CA, Jun. 2003, 43 pages.
Municipal Water Treatment, compiled Jul. 26, 2011, 7 pages.
Municipal Water Treatment—> Potable Water: Adding Fluoride, compiled Jul. 26, 2011, 5 pages.
Official Action for U.S. Appl. No. 12/814,006, mailed Dec. 30, 2011.
U.S. Appl. No. 13/159,179, filed Jun. 13, 2011, Burba et al.
U.S. Appl. No. 13/205,543, filed Aug. 8, 2011, Burba et al.
U.S. Appl. No. 13/244,092, filed Sep. 23, 2011, Hassler et al.
U.S. Appl. No. 13/244,117, filed Sep. 23, 2011, Burba et al.
Friend-Gray, "An Appetite for Apatite: A Study of Black Apatite Adsorption Effects on Organic and Non-Organic Environmental Contaminants," INQUIRY Journal, Spring 2008, at http://www.unh.edu/inquiryjournal/08/articles/friendgray.html, 6 pages.
Magalhães, "Arsenic. An environmental problem limited by solubility," Pure Appl. Chem., 2002, vol. 74(10), pp. 1843-1850.
PhosGuard Product Description, at http://www.seachem.com/Products/product_pages/PhosGuard.html, copyright 2007-2011, 2 pages.
Product Sheet for FXPb1 Carbon Filters, Filtrex Technologies Pvt. Ltd, dated unknown, 2 pages.
Tokunaga et al., "Removal of fluoride ions from aqueous solutions by multivalent metal compounds," International Journal of Environmental Studies, 1995, vol. 48(1), pp. 17-28.
International Search Report for International (PCT) Application No. PCT/US08/81079, mailed Dec. 22, 2008.
Written Opinion for International Application (PCT) No. PCT/US08/81079, mailed Dec. 22, 2008.
International Preliminary Report on Patentability for International (PCT) Patent Application No. PCT/US08/81079, mailed May 14, 2010.
Examination Report for Bangladesh Application No. 287/2008, dated Mar. 13, 2009.
Notice of Allowance for Bangladesh Patent Application No. 286/2008, dated Nov. 11, 2009.
Notice of Allowance for Bangladesh Patent Application No. 233/2009, dated Nov. 22, 2009.
Official Action (translation only) for Chinese Patent Application No. 200880123682.8, issued Sep. 8, 2011.
Official Action (including translation) for Mexican Patent Application No. MX/A/2010/004589, dated Jun. 8, 2011.
Extended European Search Report for European Patent Application No. 08845814.6, dated Jun. 6, 2011.
International Search Report for International Application No. PCT/US2008/081092, mailed Mar. 16, 2009.
Written Opinion for International Application No. PCT/US2008/081092, mailed Mar. 16, 2009.
International Preliminary Report on Patentability for International (PCT) Patent Application No. PCT/US2008/081092, mailed May 14, 2010.
Examination Report for Bangladesh Application No. 286/2008, dated Mar. 13, 2009.
Notice of Allowance for Bangladesh Patent Application No. 222/2009, dated Dec. 7, 2009.
International Search Report for International Application No. PCT/US2008/081075, mailed Mar. 9, 2009.
International Preliminary Report on Patentability for International (PCT) Patent Application No. PCT/US2008/081075, mailed May 14, 2010.
Examination Report for Bangladesh Application No. 288/2008, dated Mar. 13, 2009.
Notice of Allowance for Bangladesh Patent Application No. 221/2009, dated Dec. 7, 2009.
Restriction Requirement for U.S. Appl. No. 11/932,702, mailed Oct. 8, 2010.
Official Action for U.S. Appl. No. 11/932,702, mailed Dec. 23, 2010.
Official Action for U.S. Appl. No. 11/932,702, mailed Jun. 8, 2011.
Official Action for U.S. Appl. No. 11/931,616, mailed Feb. 18, 2010.
Official Action for U.S. Appl. No. 11/931,616, mailed Jul. 30, 2010.
Official Action for U.S. Appl. No. 11/931,616, mailed Feb, 18, 2011.
Official Action for U.S. Appl. No. 11/931,616, mailed Jul. 11, 2011.
Official Action for U.S. Appl. No. 12/814,006, mailed Jun. 28, 2011.
Official Action for U.S. Appl. No. 12/814,032, mailed Jun. 24, 2011.
Official Action for U.S. Appl. No. 12/814,049, mailed Jun. 23, 2011.
Official Action for U.S. Appl. No. 11/932,543, mailed Feb. 5, 2010.
Official Action for U.S. Appl. No. 11/932,543, mailed Jul. 29, 2010.
Official Action for U.S. Appl. No. 11/932,543, mailed Feb. 17, 2011.
Official Action for U.S. Appl. No. 11/932,543, mailed Jul. 8, 2011.
Official Action (Restriction Requirement) for U.S. Appl. No. 12/721,233, mailed Apr. 6, 2011.
Official Action for U.S. Appl. No. 12/721,233, mailed Jun. 24, 2011.
Notice of Allowance for U.S. Appl. No. 11/932,702, mailed Feb. 15, 2012.
Official Action for U.S. Appl. No. 12/814,032, mailed Feb. 29, 2012.
Official Action for U.S. Appl. No. 12/814,049, mailed Feb. 24, 2012.
Extended European Search Report for European Patent Application No. 08843496.4, dated Jan. 31, 2012.
Official Action (including translation) for Mexican Patent Application No. MX/A/2010/004589, dated Feb. 15, 2012.

* cited by examiner

US 8,252,087 B2

PROCESS AND APPARATUS FOR TREATING A GAS CONTAINING A CONTAMINANT

FIELD OF THE INVENTION

The invention relates generally to the field of fluid treatment, and primarily to processes and apparatuses for treating gases. In its more particular aspects, the invention relates to processes, apparatuses, and articles for treating breathing gases such as air that contain a chemical and/or biological contaminant.

BACKGROUND OF THE INVENTION

In light of the recent rise in terrorism, governments around the world have become increasingly concerned about the effects of chemical warfare agents, biological agents, industrial chemicals and other highly toxic materials. Because nations stockpile such materials for both industrial uses and as warfare agents, such biological and chemical contaminants represent a potential hazard to armed forces and civilian populations alike, through direct exposure and through environmental contamination.

Commonly known chemical warfare agents include organosulfur-based compounds such as 2,2'-Dichlorodiethyl sulfide (HD, mustard, mustard gas, S mustard or sulfur mustard), which are known as "blister" or "blistering" agents and can be lethal in high doses. Other chemical warfare agents include organophosphorus-based ("OP") compounds, such as O-ethyl S-(2-diisopropylamino)ethyl methylphosphonothiolate (VX), 2-Propyl methylphosphonofluoridate (GB or Sarin), and 3,3'-Dimethyl-2-butyl methylphosphonolluoridate (GD or Soman), which are commonly referred to as "nerve" agents because they attack the central nervous system and can cause paralysis and potentially death in a short period of time. Other chemical contaminants include certain industrial chemicals, insecticides and pesticides such as parathion, paraoxon and malathion, which can also have harmful effects.

Methods and materials for decontaminating surfaces exposed to such warfare agents are known in the art. Yang et al., "Decontamination of Chemical Warfare Agents", *Chem. Rev.* Vol. 92, pp 1729-1743 (1992). These decontaminant solutions and materials tend to function by chemically reacting with and/or adsorbing the agents. Early chemical-based decontaminants included bleaching powders, potassium permanganate, superchlorinated bleaches, and solutions containing alkali salts such as sodium carbonate, sodium hydroxide and potassium hydroxide. Many of these decontaminant compositions tend to have certain undesirable properties, including corrosiveness, flammability and toxicity. Additionally, some chemical-based decontaminants degrade upon exposure to water and carbon dioxide, requiring that the solution be prepared and used contemporaneously with its use.

Much of the research to date concerning biological and chemical agents has focused on the immediate need to decontaminate the surfaces that have been exposed to the agent. As a result, while the methods and compositions are designed for decontaminating vehicles, equipment, personnel and the like, they are not well suited or effective at removing, deactivating or detoxifying biological and chemical contaminants in air or other breathing gases.

Basic methods used to control air quality have included physical filtration, absorption on solid sorbents such as activated carbon, electrostatic precipitation, chemical conversion such as through the use of ozone, and treatment with various forms of radiation including heat, ultraviolet light and microwave. Filtration methods tend to be limited by the pore size of the filters, and are generally not capable of removing many biological and chemical contaminants. Moreover, ultra small pore sizes and clogging due to particulates on the filter can cause an unacceptable pressure drop across the filter for many applications. Electrostatic precipitation of particles works by charging the particles and then removing them from a gas stream onto an oppositely charged surface such as on a collection plate. This technique is not suitable for high velocity gas streams, for fluids containing volatile chemical contaminants or contaminants that are otherwise difficult to charge. Chemical reaction such as through the use of ozone is typically effective on only small volumes of gas and is impractical for many applications. Heating, although effective for removing many types of biological and chemical contaminants from gas, tends to be ineffective on higher velocity gas streams. Ultraviolet light is also effective but can be difficult to implement on larger gas volumes as the light tends to only be effective on those contaminants in the portion of the gas stream immediately adjacent the light source.

Adsorption of gases by sorbents can be effective where the sorbent is specifically matched to the gases. For example, activated carbon requires that carbon particle characteristics be matched to the properties of the gases to be adsorbed. However, what is needed is a solid sorbent that is capable of sorbing a diverse set of biological and chemical contaminants such as bacteria, viruses, nerve agents, blister agents, pesticides, insecticides and other highly toxic chemical agents from various gases, which can easily be incorporated into a variety of gas treating apparatuses.

SUMMARY OF THE INVENTION

In one embodiment, the invention provides a process for treating a gas containing one or more of a chemical and biological contaminant. The process includes contacting a gas containing one or more of a chemical or active biological contaminant with an aggregate composition at a temperature of less than about 200° C. to yield a gas depleted of chemical and active biological contaminants. The aggregate composition comprises an insoluble rare earth-containing compound and comprises no more than two elements selected from the group consisting of yttrium, scandium, and europium when the aggregate composition has been sintered. In some embodiments, the gas contacts the aggregate composition at a temperature less than about 150° C., in some cases, less than about 120° C. and in still other cases, less than about 100° C.

Optionally, the process can include one or more of the steps of separating the gas depleted of chemical and active biological contaminants from the aggregate composition, sensing the gas depleted of chemical and active biological contaminants, intermittently replacing the aggregate composition, and sterilizing the aggregate composition by treating the aggregate composition with one or more of heat, radiation and a chemical agent.

The aggregate composition can comprise aggregated particulates disposed in one or more of a fixed bed, a fluidized bed, a stirred tank and a filter. The aggregated particulates can have a mean aggregate size of at least about 1 μm. The aggregate composition can be disposed in a container, such that the gas contacts the composition by flowing through the composition. Such a container can be adapted to be removable with the process further comprising intermittently replacing the removable container. In some embodiments, the aggregate composition is incorporated into a filter.

The aggregate composition can include more than 10.01% by weight of the insoluble rare earth-containing compound and in some embodiments can include more than 95% by weight of the insoluble rare earth-containing compound. The insoluble rare earth-containing compound can include one or more of cerium, lanthanum, or praseodymium amongst other rare earth-containing compounds. When the insoluble rare earth-containing compound comprises a cerium-containing compound, the cerium-containing compound can be derived from thermal decomposition of a cerium carbonate, decomposition of a cerium oxalate, and/or from precipitation of a cerium salt. The insoluble rare earth-containing compound can include a cerium oxide, and in some cases, the aggregate composition can consists essentially of one or more cerium oxides, and optionally, one or more of a binder or flow aid. The insoluble rare earth-containing compound can comprise particulates having a mean surface area of at least about 1 $m^2/g$. The insoluble rare earth-containing compound can comprise particulates having a mean particle size of at least about 25 nm, and in some cases, of at least about 50 nm.

The chemical contaminant can comprise one or more of an organosulfur agent, an organophosphorous agent or a mixture thereof.

In another embodiment, the invention provides an apparatus for treating a gas containing one or more of a chemical and biological contaminant. The apparatus includes a container having a fluid flow path, and an aggregate composition disposed in the fluid flow path. The aggregate composition comprises at least about 5% by weight of an insoluble rare earth-containing compound and includes no more than two elements selected from the group consisting of yttrium, scandium, and europium when the aggregate composition has been sintered.

The apparatus can optionally include one or more of a filter disposed in the fluid flow path downstream of the aggregate composition, a visual indicator for indicating when the aggregate composition should be replaced, a sensor for sensing an effluent flowing out of the container, and means for sterilizing the aggregate composition. Means for sterilizing the composition can include one or more of means for heating the aggregate composition, means for irradiating the aggregate composition and means for introducing a chemical agent into the fluid flow path. The aggregate composition is disposed in the container such that the gas contacts the composition by flowing through the composition. The container can be adapted to be removable from the apparatus. Such a container can have an inlet and outlet with each of the inlet and the outlet adapted to be sealed when removed from the apparatus. The container can include one or more of a fixed bed, a fluidized bed, a stirred tank and a filter.

The aggregate composition can include more than 10.01% by weight of the insoluble rare earth-containing compound and can include more than 95% by weight of the insoluble rare earth-containing compound. The insoluble rare earth-containing compound can include one or more of cerium, lanthanum, or praseodymium amongst other rare earth-containing compounds. When the insoluble rare earth-containing compound comprises a cerium-containing compound, the cerium-containing compound can be derived from thermal decomposition of a cerium carbonate, decomposition of a cerium oxalate, and/or from precipitation of a cerium salt. The insoluble rare earth-containing compound can include a cerium oxide and in some cases, the aggregate composition can consists essentially of one or more cerium oxides, and optionally, one or more of a binder and flow aid. The insoluble rare earth-containing compound can comprise particulates having a surface area of at least about 1 $m^2/g$. The insoluble rare earth-containing compound can comprise particulates having a mean particle size of at least about 25 nm, and in some cases, of at least about 50 nm. The aggregate composition can comprise aggregated particulates having a mean aggregate size of at least about 1 μm. In some embodiments, the aggregate composition is incorporated into a filter.

In a further embodiment, the invention provides an article. The article includes a container having one or more walls defining an interior space and a flowable aggregate composition disposed in the interior space. The flowable aggregate composition includes an insoluble rare earth-containing compound and includes no more than two elements selected from the group consisting of yttrium, scandium, and europium when the composition has been sintered. The container bears instructions for use of the flowable aggregate composition to treat a gas containing one or more of a chemical and biological contaminant.

The flowable aggregate composition can include more than 10.01% by weight of the insoluble rare earth-containing compound and can include more than 95% by weight of the insoluble rare earth-containing compound. The insoluble rare earth-containing compound can include one or more of cerium, lanthanum, or praseodymium amongst other rare earth-containing compounds. When the insoluble rare earth-containing compound comprises a cerium-containing compound, the cerium-containing compound can be derived from thermal decomposition of a cerium carbonate, decomposition of a cerium oxalate, and/or from precipitation of a cerium salt. The insoluble rare earth-containing compound can include a cerium oxide and in some cases, the flowable aggregate composition can consists essentially of one or more cerium oxides, and optionally, one or more of a binder and flow aid. The insoluble rare earth-containing compound can comprise particulates having a surface area of at least about 1 $m^2/g$. The insoluble rare earth-containing compound can comprise particulates having a mean particle size of at least about 25 nm, and in some cases, of at least about 50 nm. The flowable aggregate composition can comprise aggregated particulates having a mean aggregate size of at least about 1 μm.

In another embodiment, the invention provides a filter for treating a gas containing one or more of a chemical and biological contaminant. The filter includes a filter substrate, and an aggregate composition disposed on the filter substrate.

The filter substrate can comprise one or more materials selected from the group consisting of polymers, ceramics, metals, carbons, minerals, and clays. More specifically, when the filter substrate comprises a polymer the polymer can comprise one or more materials selected from the group consisting of thermosetting polymers, thermoplastic polymers, elastomeric polymers, cellulosic polymers, and glasses. The filter substrate can also comprise an aggregate of one or more of fibers and particulates. The filter substrate can be in the form of one or more of a monolith, fabric and mat. In one embodiment, the aggregate composition comprises aggregated particulates adhered to or embedded in an outer surface of the filter substrate.

The aggregate composition can include more than 10.01% by weight of the insoluble rare earth-containing compound and can include more than 95% by weight of the insoluble rare earth-containing compound. The insoluble rare earth-containing compound can include one or more of cerium, lanthanum, or praseodymium amongst other rare earth-containing compounds. When the insoluble rare earth-containing compound comprises a cerium-containing compound, the cerium-containing compound can be derived from thermal decomposition of a cerium carbonate, decomposition of a cerium oxalate, and/or from precipitation of a cerium salt. The insoluble rare earth-containing compound can include a cerium oxide and in some cases, the aggregate can consists essentially of one or more cerium oxides, and optionally, one or more of a binder and flow aid. The insoluble rare earth-containing compound can comprise particulates having a surface area of at least about 1 $m^2/g$. The insoluble rare earth-containing compound can comprise particulates having a mean particle size of at least about 25 nm, and in some cases, of at least about 50 nm. The aggregate composition can comprise aggregated particulates having a mean aggregate size of at least about 1 µm.

DETAILED DESCRIPTION OF THE PREFERRED EMBODIMENTS

Illustrative embodiments of the invention are described below. In the interest of clarity, not all features of an actual embodiment are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover it will be appreciated that such a development effort might be complex and time-consuming, but would nevertheless be a routine undertaking for those of ordinary skill in the art having the benefit of this disclosure.

It will be understood that a process, apparatus or article as described herein can be used to remove, deactivate or detoxify biological and chemical contaminants in a gas, and in particular from breathable gases such as air. There may be a need to treat gases containing such contaminants in open environments such as on the battlefield, in enclosed spaces such as in buildings or similar structures, within vehicles such as airplanes, space craft, ships or military vehicles, and wherever such contaminants may be found. The described processes, apparatuses and articles can be used to remove, deactivate or detoxify such contaminants from gases having diverse volume and flow rate characteristics and can be applied in variety of fixed, mobile and portable applications. By way of example, such applications can include air treatment systems for buildings, vehicles, and personal breathing apparatuses for use by civilian and military personnel alike.

As used herein, "one or more of" and "at least one of" when used to preface several elements or classes of elements such as X, Y and Z or $X_1$-$X_n$, $Y_1$-$Y_n$ and $Z_1$-$Z_n$, is intended to refer to a single element selected from X or Y or Z, a combination of elements selected from the same class (such as $X_1$ and $X_2$), as well as a combination of elements selected from two or more classes (such as $Y_1$ and $Z_n$).

The terminology "remove" or "removing" includes the sorption, precipitation, conversion and killing of pathogenic and other microorganisms, such as bacteria, viruses, fungi and protozoa and chemical contaminants that may be present in a gas. The terms "deactivate" or "deactivation", "detoxify" or "de-toxification" and "neutralize" include rendering a biological or chemical contaminant non-pathogenic or benign to humans or other animals such as for example by killing the microorganisms or converting the chemical agent into a non-toxic form or species.

The terms "biological contaminant", "microbe", "microorganism", and the like include bacteria, fungi, protozoa, viruses, algae and other biological entities and pathogenic species that can be found in gases. Specific non-limiting examples of biological contaminants can include bacteria such as *Escherichia coli, Streptococcus faecalis, Shigella* spp, *Leptospira, Legimella pneumophila, Yersinia enterocolitica, Staphylococcus aureus, Pseudomonas aeruginosa, Klebsiella terrigena, Bacillus anthracis, Vibrio cholerae* and *Salmonella typhi,* viruses such as hepatitis A, noroviruses, rotaviruses, and enteroviruses, protozoa such as *Entamoeba histolytica, Giardia, Cryptosporidium parvum* and others. Biological contaminants can also include various species such as fungi or algae that are generally non-pathogenic but which are advantageously removed. How such biological contaminants came to be present in the gas, either through natural occurrence or through intentional or unintentional contamination, is non-limiting of the invention.

The term "chemical contaminant" or "chemical agent" includes known chemical warfare agents and industrial chemicals and materials such as pesticides, insecticides and fertilizers. In some embodiments, the chemical contaminant can include one or more of an organosulfur agent, an organophosphorous agent or a mixture thereof. Specific non-limiting examples of such agents include o-alkyl phosphonofluoridates, such as sarin and soman, o-alkyl phosphoramidocyanidates, such as tabun, o-alkyl, s-2-dialkyl aminoethyl alkylphosphonothiolates and corresponding alkylated or protonated salts, such as VX, mustard compounds including, 2-chloroethylchloromethylsulfide, bis(2-chloroethyl)sulfide, bis(2-chloroethylthio)methane, 1,2-bis(2-chloroethylthio)ethane, 1,3-bis(2-chloroethylthio)-n-propane, 1,4-bis(2-chloroethylthio)-n-butane, 1,5-bis(2-chloroethylthio)-n-pentane, bis(2-chloroethylthiomethyl) ether, and bis(2-chloroethylthioethyl)ether, Lewisites, including 2-chlorovinyldichloroarsine, bis(2-chlorovinyl) chloroarsine, tris(2-chlorovinyl)arsine, bis(2-chloroethyl) ethylamine, and bis(2-chloroethyl)methylamine, saxitoxin, ricin, alkyl phosphonyldifluoride, alkyl phosphonites, chlorosarin, chlorosoman, amiton, 1,1,3,3,3-pentafluoro-2-(trifluoromethyl)-1-propene, 3-quinuclidinyl benzilate, methylphosphonyl dichloride, dimethyl methylphosphonate, dialkyl phosphoramide dihalides, alkyl phosphoramidates, diphenyl hydroxyacetic acid, quinuclidin-3-ol, dialkyl aminoethyl-2-chlorides, dialkyl aminoethane-2-ols, dialkyl aminoethane-2-thiols, thiodiglycols, pinacolyl alcohols, phosgene, cyanogen chloride, hydrogen cyanide, chloropicrin, phosphorous oxychloride, phosphorous trichloride, phosphorus pentachloride, alkyl phosphorous oxychloride, alkyl phosphites, phosphorous trichloride, phosphorus pentachloride, alkyl phosphites, sulfur monochloride, sulfur dichloride, and thionyl chloride.

Non-limiting examples of industrial chemical and materials that may be effectively treated with the compositions described herein including materials that have anionic functional groups such as phosphates, sulfates and nitrates, and electro-negative functional groups, such as chlorides, fluorides, bromides, ethers and carbonyls. Specific non-limiting examples can include acetaldehyde, acetone, acrolein, acrylamide, acrylic acid, acrylonitrile, aldrin/dieldrin, ammonia, aniline, arsenic, atrazine, barium, benzidine, 2,3-benzofuran, beryllium, 1,1'-biphenyl, bis(2-chloroethyl)ether, bis(chloromethyl)ether, bromodichloromethane, bromoform, bromomethane, 1,3-butadiene, 1-butanol, 2-butanone, 2-butoxyethanol, butraldehyde, carbon disulfide, carbon tetrachloride, carbonyl sulfide, chlordane, chlordecone and mirex, chlorfenvinphos, chlorinated dibenzo-p-dioxins (CDDs), chlorine, chlorobenzene, chlorodibenzofurans (CDFs), chloroethane, chloroform, chloromethane, chlorophenols, chlorpyrifos, cobalt, copper, creosote, cresols, cyanide, cyclohexane, DDT, DDE, DDD, DEHP, di(2-ethylhexyl)phthalate, diazinon, dibromochloropropane, 1,2-dibromoethane, 1,4-dichlorobenzene, 3,3'-dichlorobenzidine, 1,1-dichloroethane, 1,2-dichloroethane, 1,1-dichloroethene, 1,2-dichloroethene, 1,2-dichloropropane, 1,3-dichloropropene, dichlorvos, diethyl phthalate, diisopropyl methylphosphonate, di-n-butylphtalate, dimethoate, 1,3-dinitrobenzene, dinitrocresols, dinitrophenols, 2,4- and 2,6-dinitrotoluene, 1,2-diphenylhydrazine, di-n-octylphthalate (DNOP), 1,4-dioxane, dioxins, disulfoton, endosulfan, endrin, ethion, ethylbenzene, ethylene oxide, ethylene glycol, ethylparathion, fenthions, fluorides, formaldehyde, freon 113, heptachlor and heptachlor epoxide, hexachlorobenzene, hexachlorobutadiene, hexachlorocyclohexane, hexachlorocyclopentadiene, hexachloroethane, hexamethylene diisocyanate, hexane, 2-hexanone, HMX (octogen), hydraulic fluids, hydrazines, hydrogen sulfide, iodine, isophorone, malathion, MBOCA, methamidophos, methanol, methoxychlor, 2-methoxyethanol, methyl ethyl ketone, methyl isobutyl ketone, methyl mercaptan, methylparathion, methyl t-butyl ether, methylchloroform, methylene chloride, methylenedianiline, methyl methacrylate, methyl-tert-butyl ether, mirex and chlordecone, monocrotophos, N-nitrosodimethylamine, N-nitrosodiphenylamine, N-nitrosodin-propylamine, naphthalene, nitrobenzene, nitrophenols, perchloroethylene, pentachlorophenol, phenol, phosphamidon, phosphorus, polybrominated biphenyls (PBBs), polychlorinated biphenyls (PCBs), polycyclic aromatic hydrocarbons (PAHs), propylene glycol, phthalic anhydride, pyrethrins and pyrethroids, pyridine, RDX (cyclonite), selenium, styrene, sulfur dioxide, sulfur trioxide, sulfuric acid, 1,1,2,2-tetrachloroethane, tetrachloroethylene, tetryl, thallium, tetrachloride, trichlorobenzene, 1,1,1-trichloroethane, 1,1,2-trichloroethane, trichloroethylene (TCE), 1,2,3-trichloropropane, 1,2,4-trimethylbenzene, 1,3,5-trinitrobenzene, 2,4,6-trinitrotoluene (TNT), vinyl acetate, and vinyl chloride.

In one embodiment of the invention, a process is provided for treating a gas containing one or more of a chemical and biological contaminant. The process includes contacting a gas containing one or more chemical and active biological contaminant with an aggregate composition at a temperature of less than about 200° C. The aggregate composition comprises an insoluble rare earth-containing compound and comprises no more than two elements selected from the group consisting of yttrium, scandium, and europium when the aggregate composition has been sintered. Contact by and between the gas and the aggregate composition removes, deactivates and/or detoxifies chemical and biological contaminants in the gas to yield a gas depleted of chemical and active biological contaminants.

Aggregate compositions suitable for use in such a process comprise an insoluble rare earth-containing compound. As used herein, "insoluble" is intended to refer to materials that are insoluble in water, or at most, are sparingly soluble in water under standard conditions of temperature and pressure.

The aggregate composition can comprises more than 10.01% by weight of the insoluble rare earth-containing compound. The amount of insoluble rare earth-containing compound can constitute more than about 11%, more than about 12% or more than about 15% by weight of the aggregate composition. In some cases a higher concentrations of rare earth compounds may be desirable. Depending on the application and the nature of other components in the aggregate composition, the composition can constitute at least about 20%, in other cases at least about 50%, in still others at least about 75%, and in yet still others more than 95%, by weight of an insoluble rare earth-containing compound.

The insoluble rare earth-containing compound can include one or more of the rear earths including lanthanum, cerium, praseodymium, neodymium, promethium, samarium, europium, gadolinium, terbium, dysprosium, holmium erbium, thulium, ytterbium and lutetium. In some embodiments, the insoluble rare-earth containing compound can comprise one or more of cerium, lanthanum, or praseodymium. Insoluble rare earth-containing compounds are available commercially and may be obtained from any source or through any process known to those skilled in the art. The aggregate composition need not include a single rare earth-containing compound but can include two or more insoluble rare earth-containing compounds. Such compounds can contain the same or different rare earth elements and can contain mixed valence or oxidation states. By way of example, when the insoluble rare earth-containing compound comprises cerium, the aggregate composition can comprise one or more cerium oxides such as $CeO_2$ (IV) and $Ce_2O_3$ (III).

In an embodiment where the insoluble rare earth-containing compound comprises a cerium-containing compound, the cerium-containing compound can be derived from precipitation of a cerium salt. In another embodiment, an insoluble cerium-containing compound can be derived from a cerium carbonate or a cerium oxalate. More specifically, an insoluble cerium-containing compound can be prepared by thermally decomposing a cerium carbonate or oxalate at a temperature between about 250° C. and about 350° C. in a furnace in the presence of air. The temperature and pressure conditions may be altered depending on the composition of the cerium-containing starting materials and the desired physical properties of the insoluble cerium-containing compound. The reaction may be summarized as:

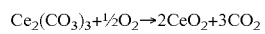

$$Ce_2(CO_3)_3 + \tfrac{1}{2}O_2 \rightarrow 2CeO_2 + 3CO_2$$

The product may be acid treated and washed to remove remaining carbonate. Thermal decomposition processes for producing cerium oxides having various features are described in U.S. Pat. No. 5,897,675 (specific surface areas), U.S. Pat. No. 5,994,260 (pores with uniform lamellar structure), U.S. Pat. No. 6,706,082 (specific particle size distribution), and U.S. Pat. No. 6,887,566 (spherical particles), and such descriptions are incorporated herein by reference. Cerium carbonate and materials containing cerium carbonate are commercially available and may be obtained from any source known to those skilled in the art.

In embodiments where the insoluble rare earth-containing compound comprises a cerium-containing compound, the insoluble cerium-containing compound can include a cerium oxide such as $CeO_2$. In a particular embodiment, the aggregate composition can consist essentially of one or more cerium oxides, and optionally, one or more of a binder and a flow aid.

The insoluble rare earth-containing compound can be present in the aggregate composition in the form of one or more of a granule, crystal, crystallite, particle or other particulate, referred to generally herein as a "particulate." The particulates of the insoluble rare earth-containing compounds can have a mean particle size of at least about 0.5 nm ranging up to about 1 μm or more. Specifically, such particulates can have a mean particle size of at least about 0.5 nm, in some cases greater than about 1 nm, in other cases, at least about 5 nm, and still other cases at least about 10 nm, and in yet still other cases at least about 25 nm. In other embodiments, the particulates can have mean particle sizes of at least about 100 nm, specifically at least about 250 nm, more specifically at least about 500 nm, and still more specifically at least about 1 μm.

To promote interaction of the insoluble rare earth-containing compound with a contaminant in a gas, the aggregate composition can comprise aggregated particulates of the insoluble rare earth-containing compound having a mean surface area of at least about 1 m²/g. Depending upon the application, higher surface areas may be desired. Specifically, the aggregated particulates can have a surface area of at least about 5 m²/g, in other cases more than about 10 m²/g, in other cases more than about 70 m²/g, in other cases more than about 85 m²/g, in still other cases more than 115 m²/g, and in yet other cases more than about 160 m²/g. In addition, it is envisioned that particulates with higher surface areas will be effective. One skilled in the art will recognize that the surface area of the aggregate composition will impact the fluid dynamics of the gas. As a result, there may be a need to balance benefits that are derived from increased surface areas with disadvantages such as pressure drop that may occur.

Optional components that are suitable for use in the aggregate composition can include one or more soluble rare earth-containing compounds, decontamination agents, biocidal agents, adsorbents, flow aids, binders, substrates, and the like. Such optional components may be included in the aggregate composition depending on the intended utility and/or the desired characteristics of the composition.

Optional soluble rare earth-containing compounds can have different activities and effects. By way of example, some soluble rare earth-containing compounds have been recognized as having a bacteriostatic or antimicrobial effect. Cerium chloride, cerium nitrate, anhydrous ceric sulfate, and lanthanum chloride are described as having such activity in "The Bacteriostatic Activity of Cerium, Lanthanum, and Thallium", Burkes et al., Journal of Bateriology, 54:417-24 (1947). Similarly, the use of soluble cerium salts such as cerium nitrates, cerous acetates, cerous sulfates, cerous halides and their derivatives, and cerous oxalates are described for use in burn treatments in U.S. Pat. No. 4,088,754, such descriptions being incorporated herein by reference. Other soluble rare earth-containing compounds, whether organic or inorganic in nature, may impart other desirable properties to the compositions and may optionally be used.

Optional decontamination agents may include materials that are capable of removing or detoxifying chemical contaminants from various surfaces. Non-limiting examples of decontamination agents that may be suitable include transition metals and alkaline metals as described in U.S. Pat. No. 5,922,926, polyoxometallates as described in U.S. Patent Application Publication No. 2005/0159307 A1, aluminum oxides as described in U.S. Pat. Nos. 5,689,038 and 6,852903, quaternary ammonium complexes as described in U.S. Pat. No. 5,859,064, zeolites as described in U.S. Pat. No. 6,537,382, and enzymes as described in U.S. Pat. No. 7,067,294. The descriptions of these decontamination agents in the noted references are incorporated herein by reference.

Biocidal agents can optionally be included for targeting biological contaminants in the gas. Suitable biocidal materials may include but are not limited to alkali metals, alkaline earth metals, transition metals, actinides, and derivatives and mixtures thereof. Specific non-limiting examples of secondary biocidal agents include elemental or compounds of silver, zinc, copper, iron, nickel, manganese, cobalt, chromium, calcium, magnesium, strontium, barium, boron, aluminum, gallium, thallium, silicon, germanium, tin, antimony, arsenic, lead, bismuth, scandium, titanium, vanadium, yttrium, zirconium, niobium, molybdenum, technetium, ruthenium, rhodium, palladium, cadmium, indium, hafnium, tantalum, tungsten, rhenium, osmium, iridium, platinum, gold, mercury, thallium, thorium, and the like. Derivatives of such agents can include acetates, ascorbates, benzoates, carbonates, carboxylates, citrates, halides, hydroxides, gluconates, lactates, nitrates, oxides, phosphates, propionates, salicylates, silicates, sulfates, sulfadiazines, and combinations thereof. When the aggregate composition optionally comprises a titanium-containing compound such as a titanium oxide, the weight ratio of the titanium-containing compound to the insoluble rare earth-containing compound is less than about 2:1. When the aggregate composition optionally comprises an aluminum-containing compound, the weight ratio of the aluminum-containing compound to the insoluble rare earth-containing compound is less than about 10:1. In an embodiment that includes an optional biocide agent selected from the group consisting of transition metals, transition metal oxides and transition metal salts, the aggregate composition will comprise less than about 0.01% by weight of a mixture of silver and copper metal nanoparticles.

Other materials that may be suitable for use as biocidal agents include organic agents such as quaternary ammonium salts as described in U.S. Pat. No. 6,780,332, and organosilicon compounds such as are described in U.S. Pat. No. 3,865,728. Other organic materials and their derivatives that are known to deactivate biological contaminants may also be used. By way of example, polyoxometalates are described in U.S. Pat. No. 6,723,349 as being effective at removing biological contaminants from fluids. This patent references M. T. in Heteropoly and Isopoly Oxometalates, Springer Verlag, 1983, and Chemical Reviews, vol. 98, No. 1, pp. 1-389, 1998, as describing examples of effective polyoxometalates. The descriptions of these organic biocidal agents in the noted references are incorporated herein by reference.

The aggregate composition may optionally comprise one or more flow aids. Flow aids are used in part to improve the fluid dynamics of a fluid over or through the aggregate composition, to prevent separation of components of the aggregate composition, prevent the settling of fines, and in some cases to hold the aggregate composition in place. Suitable flow aids can include both organic and inorganic materials. Inorganic flow aids can include ferric sulfate, ferric chloride, ferrous sulfate, aluminum sulfate, sodium aluminate, polyaluminum chloride, aluminum trichloride, silicas, diatomaceous earth and the like. Organic flow aids can include organic flocculents known in the art such as polyacrylamides (cationic, nonionic, and anionic), EPI-DMA's (epichlorohydrin-dimethylamines), DADMAC's (polydiallydimethylammonium chlorides), dicyandiamide/formaldehyde polymers, dicyandiamide/amine polymers, natural guar, etc. When present, the flow aid can be mixed with the insoluble rare earth-containing compound and polymer binder during the formation of the aggregate composition. Alternatively, particulates of the aggregate composition and of the flow aid can be mixed to yield a physical mixture with the flow aid dispersed uniformly throughout the mixture. In yet another alternative, the flow aid can be disposed in one or more distinct layers upstream and downstream of the aggregate composition. When present, flow aids are generally used in low concentrations of less than about 20%, in some cases less than 15%, in other cases less than 10%, and in still other cases less than about 8% by weight of the aggregate composition.

Other optional components can include various inorganic agents including ion-exchange materials such as synthetic ion exchange resins, activated carbons, zeolites (synthetic or naturally occurring), minerals and clays such as bentonite, smectite, kaolin, dolomite, montmorillinite and their derivatives, metal silicate materials and minerals such as of the phosphate and oxide classes. In particular, mineral compositions containing high concentrations of calcium phosphates, aluminum silicates, iron oxides and/or manganese oxides with lower concentrations of calcium carbonates and calcium sulfates may be suitable. These materials may be calcined and processed by a number of methods to yield mixtures of varying compositions and properties.

A binder may optionally be included for forming an aggregate composition having desired size, structure, density, porosity and fluid properties. In addition to, or as an alternative to the use of a binder, a substrate may be included for providing support to the aggregate composition. Suitable binder and substrate materials can include any material that will bind and/or support the insoluble rare earth-containing compound wider conditions of use. Such materials will generally be included in the aggregate composition in amounts ranging from about 0 wt % to about 90 wt %, based upon the total weight of the composition. Suitable materials can include organic and inorganic materials such as natural and synthetic polymers, ceramics, metals, carbons, minerals, and clays. One skilled in the art will recognize that the selection of a binder or substrate material will depend on such factors as the components to be aggregated, their properties and binding characteristics, desired characteristics of the final aggregate composition and its method of use among others.

Suitable polymeric binders can include both naturally occurring and synthetic polymers, as well as synthetic modifications of naturally occurring polymers. In general, polymers melting between about 50° C. and about 500° C., more particularly, between about 75° C. and about 35° C., even more particularly between about 80° C. and about 200° C., are suitable for use in aggregating the components of the composition. Non-limiting examples can include polyolefins that soften or melt in the range from about 85° C. to about 180° C., polyamides that soften or melt in the range from about 200° C. to about 300° C., and fluorinated polymers that soften or melt in the range from about 300° C. to about 400° C.

Depending upon the desired properties of the composition, polymer binders can include one or more polymers generally categorized as thermosetting, thermoplastic, elastomer, or a combination thereof as well as cellulosic polymers and glasses. Suitable thermosetting polymers include, but are not limited to, polyurethanes, silicones, fluorosilicones, phenolic resins, melamine resins, melamine formaldehyde, and urea formaldehyde. Suitable thermoplastics can include, but are not limited to, nylons and other polyamides, polyethylenes, including LDPE, LLDPE, HDPE, and polyethylene copolymers with other polyolefins, polyvinylchlorides (both plasticized and unplasticized), fluorocarbon resins, such as polytetrafluoroethylene, polystyrenes, polypropylenes, cellulosic resins, such as cellulose acetate butyrates, acrylic resins, such as polyacrylates and polymethylmethacrylates, thermoplastic blends or grafts such as acrylonitrile-butadiene-styrenes or acrylonitrile-styrenes, polycarbonates, polyvinylacetates, ethylene vinyl acetates, polyvinyl alcohols, polyoxymethylene, polyformaldehyde, polyacetals, polyesters, such as polyethylene terephthalate, polyether ether ketone, and phenolformaldehyde resins, such as resols and novolacs. Suitable elastomers can include, but are not limited to, natural and/or synthetic rubbers, like styrene-butadiene rubbers, neoprenes, nitrile rubber, butyl rubber, silicones, polyurethanes, alkylated chlorosulfonated polyethylene, polyolefins, chlorosulfonated polyethylenes, perfluoroelastomers, polychloroprene (neoprene), ethylene-propylene-diene terpolymers, chlorinated polyethylene, fluoroelastomers, and ZALAK™ (Dupont-Dow elastomer). In a specific embodiment, where the polymer binder comprises an ethylene vinyl copolymer, the insoluble rare earth-containing compound consists essentially of an anhydrous rare earth-containing compound. Those of skill in the art will realize that some of the thermoplastics listed above can also be thermosets depending upon the degree of cross-linking, and that some of each may be elastomers depending upon their mechanical properties. The categorization used above is for ease of understanding and should not be regarded as limiting or controlling.

Cellulosic polymers can include naturally occurring cellulose such as cotton, paper and wood and chemical modifications of cellulose. In a specific embodiment, the insoluble rare earth-containing compound can be mixed with paper fibers or incorporated directly into paper pulp for forming a paper-based filter comprising the insoluble rare earth-containing compound.

Polymer binders can also include glass materials such as glass fibers, beads and mats. Glass solids may be mixed with particulates of an insoluble rare earth-containing compound and heated until the solids begin to soften or become tacky so that the insoluble rare earth-containing compound adheres to the glass. Similarly, extruded or spun glass fibers may be coated with particles of the insoluble rare earth-containing compound while the glass is in a molten or partially molten state or with the use of adhesives. Alternatively, the glass composition may be doped with the insoluble rare earth-containing compound during manufacture. Techniques for depositing or adhering insoluble rare earth-containing compounds to a substrate material are described in U.S. Pat. No. 7,252,694 and other references concerning glass polishing. For example, electro-deposition techniques and the use of metal adhesives are described in U.S. Pat. No. 6,319,108 as being useful in the glass polishing art. The descriptions of such techniques are incorporated herein by reference.

In some applications, water-soluble glasses such as are described in U.S. Pat. Nos. 5,330,770, 6,143,318 and 6,881,766, may be an appropriate polymer binder. The descriptions of such glasses in the noted references are incorporated herein by reference. In other applications, materials that swell through fluid absorption including but not limited to polymers such as synthetically produced polyacrylic acids, and polyacrylamides and naturally-occurring organic polymers such as cellulose derivatives may also be used. Biodegradable polymers such as polyethylene glycols, polylactic acids, polyvinylalcohols, co-polylactideglycolides, and the like may also be used as the polymer binder.

Minerals and clays such as bentonite, smectite, kaolin, dolomite, montmorillinite and their derivatives may also serve as suitable binder or substrate materials.

Where it is desirable to regenerate the aggregate composition through sterilization, the selected binder or substrate material should be stable tinder sterilization conditions and should be otherwise compatible with the sterilization method. Specific non-limiting examples of polymeric binders that are suitable for sterilization methods that involve exposure to high temperatures include cellulose nitrate, polyethersulfone, nylon, polypropylene, polytetrafluoroethylene, and mixed cellulose esters. Compositions prepared with these binders can be autoclaved when the prepared according to known standards. Desirably, the aggregate composition should be stable to steam sterilization or autoclaving as well as to chemical sterilization through contact with oxidative or reductive chemical species, as a combination of sterilization methods may be required for efficient and effective regeneration. In an embodiment where sterilization includes the electrochemical generation of an oxidative or reductive chemical species, the electrical potential necessary to generate said species can be attained by using the composition as one of the electrodes. For example, a composition that contains a normally insulative polymeric binder can be rendered conductive through the inclusion of a sufficiently high level of conductive particles such as granular activated carbon, carbon black, or metallic particles. Alternatively, if the desired level of carbon or other particles is not sufficiently high to render an otherwise insulative polymer conductive, an intrinsically conductive polymer may included in the binder material. Various glasses such as microporous glass beads and fibers are particularly suited for use as a substrate or binder where the composition is to be periodically regenerated.

Other optional components of the aggregate composition can include additives, such as particle surface modification additives, coupling agents, plasticizers, fillers, expanding agents, fibers, antistatic agents, initiators, suspending agents, photosensitizers, lubricants, wetting agents, surfactants, pigments, dyes, UV stabilizers, and suspending agents. The amounts of these materials are selected to provide the properties desired. Such additives may be incorporated into a binder or substrate material, applied as a separate coating, held within the structure of the aggregate composition, or combinations of the above.

The aggregate composition can be used to remove, deactivate or detoxify chemical and biological contaminants in a gas by contacting the fluid with the composition. Those familiar with the art of fluid treatment will understand that the composition, physical dimensions and shape of the aggregate composition may be manipulated for different applications and that variations in these variables can alter flow rates, back-pressure, and the activity of the composition for treating certain contaminants. As a result, the size, form and shape of the aggregate composition can vary considerably depending on the intended method of use.

The aggregate composition can be formed though one or more of extrusion, molding, calcining, sintering, compaction, the use of a binder or substrate, adhesives and/or other techniques known in the art. It should be noted that neither a binder nor a substrate is required in order to form the aggregate composition although such components may be desired depending on the intended application. In embodiments where the gas is to flow through a bed of the aggregate composition, the composition can incorporate a polymer binder so that the resulting composition has both high surface area and a relatively open structure. Such an aggregate composition maintains elevated activity for treating contaminants in the gas without imposing a substantial pressure drop on gas flow. In embodiments where it is desired that the aggregate composition have higher surface areas, sintering is a less desirable technique for forming the aggregate composition. As noted, when the insoluble rare earth-containing compound has been sintered to form the aggregate composition, the composition will contain no more than two elements selected from the group consisting of yttrium, scandium, and europium.

The aggregate composition can comprise aggregated particulates in granule, bead, pellet, powder, fiber, or similar form. Such aggregated particulates can have a mean aggregate size of at least about 1 μm, specifically at least about 5 μm, more specifically at least about 10 μm, and still more specifically at least about 25 μm. In other embodiments, the aggregate will have a mean aggregate size of at least about 0.1 mm, specifically at least about 0.5 mm, more specifically at least about 1 mm, still more specifically at least about 2 mm, and yet still more specifically more than 5.0 mm. The aggregate composition can be crushed, cut, chopped or milled and then sieved to obtain a desired particle size. Such aggregated particulates can be used in fixed or fluidized beds or reactors, stirred reactors or tanks, distributed in particulate filters, encapsulated or enclosed within membranes, mesh, screens, filters or other fluid permeable structures, deposited on filter substrates, and may further be formed into a desired shape such as a sheet, film, mat or monolith for various applications.

In addition, the aggregate composition can be incorporated into or coated onto a filter substrate. Suitable filter substrates can be formed from the described binder and substrate materials such as sintered ceramics, sintered metals, microporous carbon, glass fibers and beads, and cellulosic fibers such as cotton, paper and wood. The structure of the substrate will vary depending upon the application but can include woven and non-wovens in the form of a porous membrane, filter or other fluid permeable structure. Substrates can also include porous and permeable solids having a desired shape and physical dimensions. Such substrates can include mesh, screens, tubes, honeycombed structures, monoliths and blocks of various shapes including cylinders and toroids.

In other embodiments, the aggregate composition can be disposed in a container and the gas caused to flow through the composition. The gas can be pumped or drawn through the composition, with or without agitation or mixing. Various fittings, connections, pumps, valves, manifolds and the like can be used to control the flow of the gas through the composition in a given container.

The gas contacts the aggregate composition at a temperature less than about 200° C. In some cases, the gas contacts the composition at a temperature less than about 150° C., in other cases, at a temperature less than about 120° C., and in still other cases less than about but 100° C. In some embodiments, such as where the aggregate composition is incorporated into a personal breathing apparatus such as a gas mask or surgical mask, the aggregate composition contacts the gas at or about room temperature. The aggregate composition is effective at removing, deactivating, and detoxifying chemical and biological contaminants at room temperatures. The pressure at which the gas contacts the aggregate composition can vary considerably depending on the application, but again, the composition can effectively treat a gas at ambient pressures.

After contacting the gas, the aggregate composition may contain chemical and both active and deactivated biological contaminants. As a result, it may be advantageous to sterilize the composition before re-use or disposal. Moreover, it may be desirable to sterilize the composition prior to initial use to remove any biological contaminants that may be present before use. Sterilization processes can include thermal processes wherein the composition is exposed to elevated temperatures or pressures or both, radiation sterilization wherein the composition is subjected to elevated radiation levels using ultraviolet, infrared, microwave, and/or ionizing radiation, as well as chemical sterilization wherein the aggregate composition is exposed to elevated levels of oxidants, reductants or other chemical species. More specifically, chemical species that may be used in chemical sterilization can include halogens, reactive oxygen species, formaldehyde, surfactants, metals and gases such as ethylene oxide, methyl bromide, beta-propiolactone, and propylene oxide. Combinations of these processes can also be used and it should further be recognized that such sterilization processes may be used on an intermittent or continuous basis while the composition is in use.

The process can optionally include the step of sensing the gas after it has contacted the aggregate composition and is depleted of contaminants so as to determine or calculate when it is appropriate to replace the composition. Sensing of the gas can be achieved through conventional means such as tagging and detecting the contaminants in the gas, measuring flow rates, temperatures, pressures, sensing for the presence of fines, and sampling and conducting arrays.

The process can optionally include separating the gas depleted of contaminants from the composition. The composition can be separated from the gas by conventional gas-solid separation techniques including, but not limited to, the use of filters, membranes, centrifuges, cyclones or the like. The separated gas depleted of contaminants can then be directed to further processing, storage or use.

In another embodiment, the invention is directed to an apparatus for treating a gas containing one or more of a chemical or biological contaminant. The apparatus comprises a container having a fluid flow path and an aggregate composition as described herein disposed in the fluid flow path. Specifically, the aggregate composition comprises at least about 5% by weight of an insoluble rare earth-containing compound and no more than two elements selected from the group consisting of yttrium, scandium, and europium when the aggregate is sintered. Other features of the aggregate composition have been described in detail and are not repeated here.

The container can take a variety of forms including columns, various tanks and reactors, filters, filter beds, drums, cartridges, fluid permeable containers and the like. In some embodiments, the container will include one or more of a fixed bed, a fluidized bed, a stirred tank or reactor, or filter, within which the gas will contact the composition. The container can have a single pass through design with a designated fluid inlet and fluid outlet or can have fluid permeable outer wall enclosing or encapsulating the aggregate composition. Where it is desired that the container be flexible in nature, the fluid permeable outer wall can be made from woven or non-woven fabric of various materials. Where a more rigid structure is preferred, the container can be manufactured from metals, plastics such as PVC or acrylic, or other materials that will maintain a desired shape under conditions of use.

The gas can flow through the composition and container under pressure or vacuum, with or without agitation or mixing. Various fittings, connections, pumps, valves, manifolds and the like can be used to control the flow of the gas into the container and through the composition.

The container can be adapted to be inserted into and removed from an apparatus or process stream to facilitate use and replacement of the composition. Such a container can have an inlet and outlet that are adapted to be sealed when removed from the apparatus or when otherwise not in use to enable the safe handling, transport and storage of the container and composition. Where the aggregate composition is to be periodically sterilized, the composition and container may be removed and sterilized as a unit, without the need to remove the composition from the container. In addition, such a container may also be constructed to provide long term storage or to serve as a disposal unit for chemical and/or biological contaminants removed from a treated gas.

The apparatus can include a filter for separating the treated gas from the composition. The filter can encapsulate the aggregate composition or be disposed downstream of the composition. Moreover, the filter can be a feature of the container for preventing the composition from flowing out of the container or be a feature of the apparatus disposed downstream of the container. The filter can include woven and non-woven fabrics, mesh, as well as fibers or particulates that are disposed in a mat, bed or layer that provides a fluid permeable barrier to the aggregate composition. Where the aggregate composition is disposed in a fixed bed, a suitable filter can include a layer of diatomaceous earth disposed downstream of the composition within the container.

The apparatus may also optionally include one or more of a visual indicator for indicating when the composition should be replaced or regenerated, a sensor for sensing an effluent flowing out of the container, and means for sterilizing the composition. Means for sterilizing the composition can include one or more of means for heating the composition, means for irradiating the composition and means for introducing a chemical oxidation agent into the fluid flow path, such as are known in the art.

In yet another embodiment, the invention provides an article comprising a container having one or more walls defining an interior space and a flowable aggregate composition disposed in the interior space. As described in detail herein, the flowable aggregate composition comprises an insoluble rare earth-containing compound and comprises no more than two elements selected from the group consisting of yttrium, scandium, and europium when the aggregate has been sintered. In addition, the container bears instructions for use of the aggregate composition to treat a gas containing one or more of a chemical and biological contaminant. In this particular embodiment, the container is a bag or other bulk product package in which the flowable aggregate composition may be marketed or sold to retailers, distributors or end use consumers. Such containers can take a variety of sizes, shapes, and forms, but are typically made from plastics or various fabrics. The container bears an instruction indicating that the contents of the container can be effectively used to treat a gas for the purpose of removing, deactivating or detoxifying chemical and biological contaminants that may be in the gas.

In another embodiment, the invention is directed to a filter for treating a gas containing one or more of a chemical and biological contaminant. The filter comprises a filter substrate and an aggregate composition disposed on the filter substrate.

The filter substrate can comprise any of the binder and substrate materials described herein, including one or more materials selected from the group consisting of polymers, ceramics, metals, carbons, minerals, and clays. More specifically, the filter substrate can comprises one or more polymer materials selected from the group consisting of thermosetting polymers, thermoplastic polymers, elastomeric polymers, cellulosic polymers, and glasses. The filter substrate can also comprise fibers, particulates, and mixtures and aggregates of the same. Specific non-limiting examples of the filter substrate include polyolefins such as polyethylene, cellulose acetate, acrylonitrile-butadiene-styrene, PTFE, paper fibers, and fiberglass. The filter substrate can be processed into a variety of sizes and shapes including but not limited to a monolith, fabric or mat.

The aggregate composition comprises an insoluble rare earth-containing compound and no more than two elements selected from the group consisting of yttrium, scandium, and europium when the aggregate is sintered. Other features of the aggregate composition have been described in detail and are not repeated here.

In one embodiment, the aggregate composition comprises aggregated particulates adhered to or embedded in an outer surface of the filter substrate.

The filter can be used in a variety of gas treatment and air handling applications known in the art including use as filter elements in HVAC and other air handling or air filtration systems for buildings and vehicles, as well as filter elements in personal breathing apparatuses such as gas masks, surgical masks, respirators and the like.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed is:

1. A process, comprising:
contacting a contaminated gas containing one or more of a chemical and an active biological contaminant with a cerium (IV) oxide-containing aggregate composition to remove the one or more of a chemical and active biological contaminant, respectively, to form a decontaminated gas and a contacted cerium (IV) oxide-containing aggregate composition, wherein the contacted cerium (IV) oxide-containing aggregate composition comprises the one or more of the chemical and biological contaminants and wherein the cerium (IV) oxide-containing aggregate composition comprises at least about 50% by weight cerium (IV) oxide;
separating the decontaminated gas from the contacted cerium (IV) oxide-containing aggregate composition; and
sterilizing the contacted cerium (IV) oxide-containing aggregate composition to remove the one or more of a chemical and biological contaminants.

2. The process of claim 1, wherein the sterilizing comprises exposing the contacted cerium (IV) oxide-containing aggregate composition to an elevated temperature, wherein the one or more of a chemical and an active biological contaminant is the active biological contaminant, and wherein the cerium (IV) oxide-containing aggregate composition kills the active biological contaminant.

3. The process of claim 1, wherein the sterilizing comprises exposing the contacted cerium (IV) oxide-containing aggregate composition to an elevated pressure, wherein the one or more of a chemical and an active biological contaminant is the active biological contaminant, and wherein the cerium (IV) oxide-containing aggregate composition kills the active biological contaminant.

4. The process of claim 1, wherein the sterilizing comprises exposing the contacted cerium (IV) oxide-containing aggregate composition to an elevated level of radiation, the radiation being ultraviolet, microwave, and/or ionizing radiation wherein one or more of a chemical and an active biological contaminant is the active biological contaminant, and wherein the cerium (IV) oxide-containing aggregate composition kills the active biological contaminant.

5. The process of claim 1, wherein the sterilizing comprises exposing the contacted cerium (IV) oxide-containing aggregate composition to a chemical oxidant, and wherein, the one or more of a chemical and an active biological contaminant is the chemical contaminant.

6. The process of claim 1, wherein the sterilizing comprises exposing the contacted cerium (IV) oxide-containing aggregate composition to a chemical reductant and wherein the one or more of a chemical and an active biological contaminant is the chemical contaminant.

7. The process of claim 1, wherein the sterilizing comprises exposing the contacted cerium (IV) oxide-containing aggregate composition to a chemical species comprising one or more of a halogen, reactive oxygen species, formaldehyde, a surfactant, a metal other than a rare earth, and a gas selected from the group consisting of ethylene oxide, methyl bromide, beta-propiolactone, propylene oxide, and mixtures thereof.

8. The process of claim 1, further comprising:
sensing a property of the decontaminated gas to determine when to replace, the cerium (IV) oxide-containing aggregate composition, the sensing comprising one or more of a presence of the one or more of a chemical and biological contaminant in the decontaminated gas, decontaminated gas flow rate, decontaminated gas temperature, and decontaminated gas pressure.

9. The process of claim 8, wherein sensing comprises at least one of tagging and detecting the one or more of a chemical and biological contaminant in the decontaminated gas.

10. The process of claim 8, wherein sensing comprises measuring at least one of the decontaminated gas flow rate, temperature; and pressure.

11. The process of claim 8, wherein sensing is performed by a sampling and conducting array.

12. The process of claim 8, wherein sensing comprises sensing for the presence of fines in the decontaminated gas.

13. The process of claim 1, wherein the decontaminated gas is substantially depleted of the chemical and active biological contaminants, wherein the cerium (IV) oxide-containing aggregate composition further comprises one or more of cerium (III), lanthanum, neodymium, and praseodymium, and wherein the cerium (IV) oxide-containing aggregate composition comprises aggregated particulates having a mean aggregate size of at least about 25 microns.

14. A method, comprising:
(a) contacting a gas comprising a contaminant with an aggregate composition comprising cerium (IV) oxide and a different rare earth having a different oxidation state than cerium (IV) to form a treated gas substantially depleted of the contaminant, wherein:
(b) the contaminant is at least one of:
(B1) one or more of o-alkyl phosphonofluoridates, o-alkyl phosphoramidocyanidates, o-alkyl, s-2-dialkyl aminoethyl alkylphosphonothiolates, alkylated or protonated salts thereof, 2-chloroethylchloromethylsulfide, bis(2-chloroethyl)sulfide, bis(2-chloroethylthio)methane, 1,2-bis(2-chloroethylthio)ethane, 1,3-bis(2-chloroethylthio)-n-propane, 1,4-bis(2-chloroethylthio)-n-butane, 1,5-bis(2-chloroethylthio)-n-pentane, bis(2-chloroethylthiomethyl)ether, bis(2-chloroethylthioethyl)ether, bis(2-chloroethyl)ethylamine, bis(2-chloroethyl)methylamine, saxitoxin, ricin, alkyl phosphonyldifluoride, alkyl phosphonites, chlorosarin, chlorosoman, amiton, 1,1,3,3,3-pentafluoro-2-(trifluoromethyl)-1-propene, 3-quinuclidinyl benzilate, methylphosphonyl dichloride, dimethyl methylphosphonate, dialkyl phosphoramidic dihalides, alkyl phosphoramidates, diphenyl hydroxyacetic acid, quinuclidin-3-ol, dialkyl aminoethyl-2-chlorides, dialkyl aminoethane-2-ols, dialkyl aminoethane-2-thiols, thiodiglycols, pinacolyl alcohols, phosgene, cyanogen chloride, hydrogen cyanide, chloropicrin, phosphorous oxychloride, phosphorous trichloride, phosphorus pentachloride, alkyl phosphorous oxychloride, alkyl phosphites, phosphorous trichloride, phosphorus pentachloride, alkyl phosphites, sulfur monochloride, sulfur dichloride, thionyl chloride, ethers, carbonyls, acetaldehyde, acetone, acrolein, acrylamide, acrylic acid, acrylonitrile, aldrin, dieldrin, ammonia, aniline, atrazine, benzidine, 2,3-benzofuran, beryllium, 1,1'-biphenyl, bis(2-chloroethyl)ether, bis(chloromethyl)ether, bromodichloromethane, bromoform, bromomethane, 1,3-butadiene, 1-butanol, 2-butanone, 2-butoxyethanol, butraldehyde, carbon disulfide, carbon tetrachloride, carbonyl sulfide, chlordane, chlordecone, mirex, chlorfenvinphos, chlorinated dibenzo-p-dioxins (CDDs), chlorine, chlorobenzene, chlorodibenzofurans (CDFs), chloroethane, chloroform, chloromethane, chlorophenols, chlorpyrifos, creosote, cresols, cyclohexane, DDT, DDE, DDD, DEHP, di(2-ethylhexyl)phthalate, diazinon, dibromochloropropane, 1,2-dibromoethane, 1,4-dichlorobenzene, 3,3'-dichlorobenzidine, 1,1-dichloroethane, 1,2-dichloroethane, 1,1-dichloroethene, 1,2-dichloroethene, 1,2-dichloropropane, 1,3-dichloropropene, dichlorvos, diethyl phthalate, diisopropyl methylphosphonate, di-n-butylphtalate, dimethoate, 1,3-dinitrobenzene, dinitrocresols, dinitrophenols, 2,4-dinitrotoluene, 2,6-dinitrotoluene, 1,2-diphenylhydrazine, di-n-octylphthalate (DNOP), 1,4-dioxane, dioxins, disulfoton, endosulfan, endrin, ethion, ethylbenzene, ethylene oxide, ethylene glycol, ethylparathion, fenthions, formaldehyde, freon 113, heptachlor, heptachlor epoxide, hexachlorobenzene, hexachlorobutadiene, hexachlorocyclohexane, hexachlorocyclopentadiene, hexachloroethane, hexamethylene diisocyanate, hexane, 2-hexanone, HMX (octogen), hydraulic fluids, hydrazines, hydrogen sulfide, iodine, isophorone, malathion, MBOCA, methamidophos, methanol, methoxychlor, 2-methoxyethanol, methyl ethyl ketone, methyl isobutyl ketone, methyl mercaptan, methylparathion, methyl t-butyl ether, methylchloroform, methylene chloride, methylenedianiline, methyl methacrylate, methyl-tert-butyl ether, mirex, chlordecone, monocrotophos, N-nitrosodimethylamine, N-nitrosodiphenylamine, N-nitrosodi-n-propylamine, naphthalene, nitrobenzene, nitrophenols, perchloroethylene, pentachlorophenol, phenol, phosphamidon, phosphorus, polybrominated biphenyls (PBBs), polychlorinated biphenyls (PCBs), polycyclic aromatic hydrocarbons (PAHs), propylene glycol, phthalic anhydride, pyrethrins, pyrethroids, pyridine, RDX (cyclonite), selenium, styrene, sulfur dioxide, sulfur trioxide, sulfuric acid, 1,1,2,2-tetrachloroethane, tetrachloroethylene, tetryl, thallium, tetrachloride, trichlorobenzene, 1,1,1-trichloroethane, 1,1,2-trichloroethane, trichloroethylene (TCE), 1,2,3-trichloropropane, 1,2,4-trimethylbenzene, 1,3,5-trinitrobenzene, 2,4,6-trinitrotoluene (TNT), vinyl acetate, and vinyl chloride; and (B2) an active biological contaminant;

wherein:

the aggregate composition comprises a plurality of extruded aggregated particulates comprising cerium (IV) oxide-containing particles and a binder;

the aggregate composition comprises at least about 75% by weight cerium (IV)-oxide;

the extruded aggregated particulates have an average surface area of at least about 70 $m^2/g$; and the extruded aggregated particulates have a mean aggregate size of at least about 25 μm.

15. The method of claim 14, wherein the binder is one or more of a fluorosilicone, fluorocarbon resin, perfluoroelastomer, and fluoroelastomer.

16. The method of claim 14, wherein the extruded aggregated particulates do not comprise a substrate and have a mean aggregate size of at least about 0.1 mm and wherein the mean particle size of the plurality of cerium (IV) oxide-containing particles is at least about 1 μm.

17. The method of claim 14, wherein the aggregate composition comprises at least about 95% by weight cerium oxide.

18. The method of claim 14, wherein the extruded aggregated particulates have an average surface area of at least about 85 $m^2/g$.

19. The method of claim 14, wherein the aggregate composition further comprises:
a decontamination agent selected from the group consisting of transition metals, alkaline metals, polyoxometallates, quaternary ammonium complexes, zeolites, enzymes, and derivatives and mixtures thereof.

20. The method of claim 14, wherein the binder comprises one or more polymers selected from the group consisting of thermosetting polymers, thermoplastic polymers, elastomeric polymers, cellulosic polymers, glasses, and mixtures thereof and wherein the aggregate composition is adhered to or embedded in an outer surface of a filter substrate.

21. The method of claim 14, wherein the binder has a melting point between about 50 to about 500° C.

22. The method of claim 14, wherein the binder is biodegradable.

23. The method of claim 14, wherein the binder is one of a mineral and clay.

24. The method of claim 14, wherein the contaminant comprises at least one member of B1.

25. The method of claim 14, wherein the contaminant comprises B2.

26. The method of claim 14, wherein the aggregate composition comprises no more than two elements selected from the group consisting of yttrium, scandium, and europium when the aggregate composition has been sintered.

27. The method of claim 14, further comprising a flow aid selected from the group consisting of ferric sulfates, ferric chlorides, ferrous sulfates, aluminum sulfates, sodium aluminates, polyaluminum chlorides, aluminum trichlorides, silicas, diatomaceous earths, organic flocculents, and mixtures, thereof.

28. The method of claim 14, further comprising an ion-exchange material.

29. A method, comprising:

contacting a cerium (IV) oxide-containing compound with a gas to remove, from the gas, a contaminant that is one or more of 1,1,3,3,3-pentafluoro-2-(trifluoromethyl)-1-propene, phosgene, acetone, acrolein, aldrin, dieldrin, 2,3-benzofuran, bis(2-chloroethyl)ether, bis(chloromethyl)ether, bromodichloromethane, bromoform, bromomethane, 2-butanone, butraldehyde, carbon tetrachloride, chlordane, chlordecone, mirex, chlorinated dibenzo-p-dioxins (CDDs), chlorobenzene, chlorodibenzofurans (CDFs), chloroethane, chloroform, chloromethane, DDT, DDE, DDD, DEHP, di(2-ethylhexyl) phthalate, dibromochloropropane, 1,2-dibromoethane, 1,4-dichlorobenzene, 1,1-dichloroethane, 1,2-dichloroethane, 1,1-dichloroethene, 1,2-dichloroethene, 1,2-dichloropropane, 1,3-dichloropropene, diethyl phthalate, di-n-butylphtalate, di-n-octylphthalate (DNOP), 1,4-dioxane, dioxins, endrin, ethylene oxide, formaldehyde, freon 113, heptachlor, heptachlor epoxide, hexachlorobenzene, hexachlorobutadiene, hexachlorocyclohexane, hexachlorocyclopentadiene, hexachloroethane, 2-hexanone, isophorone, methoxychlor, methyl ethyl ketone, methyl isobutyl ketone, methyl t-butyl ether, methylchloroform, methylene chloride, methyl methacrylate, methyl-tert-butyl ether, perchloroethylene, polybrominated biphenyls (PBBs), polychlorinated biphenyls (PCBs), phthalic anhydride, pyrethrins, pyrethroids, 1,1,2,2-tetrachloroethane, tetrachloroethylene, tetrachloride, trichlorobenzene, 1,1,1-trichloroethane, 1,1,2-trichloroethane, trichloroethylene (TCE), 1,2,3- trichloropropane, vinyl acetate, and vinyl chloride to yield a treated gas substantially depleted of the contaminant.

30. The method of claim 29, wherein the cerium (IV) oxide-containing compound comprises at least one other rare earth selected from the group consisting of lanthanum, cerium, praseodymium, neodymium, promethium, samarium, europium, gadolinium, terbium, dysprosium, holmium, erbium, thulium, ytterbium, lutetium, and mixtures thereof and wherein the cerium (IV) and at least one other rare earth have different oxidation states.

31. The method of claim 29, wherein cerium (IV) oxide-containing compound comprises at least one other rare earth selected from the group consisting of lanthanum, cerium, praseodymium, neodymium, promethium, samarium, europium, gadolinium, terbium, dysprosium, holmium, erbium, thulium, ytterbium, lutetium, and mixtures thereof and wherein the cerium (IV) and at least one other rare earth have different valence states.

32. The method of claim 30, wherein the contaminant has an electro-negative functional group that is reactive with the cerium (IV) oxide-containing compound, and wherein the electro-negative functional group comprises at least one of chloride, fluoride, bromide, ether, and carbonyl.

33. The method of claim 31, wherein the cerium (IV) oxide-containing compound is in an aggregate composition comprising at least about 75% by weight cerium (IV) oxide.

34. A method, comprising:
(a) receiving a gas comprising a contaminant that comprises at least one of:
(A1) one or more of o-alkyl phosphonofluoridates, o-alkyl phosphoramidocyanidates, o-alkyl, s-2-dialkyl aminoethyl alkylphosphonothiolates, alkylated or protonated salts thereof, 2-chloroethylchloromethylsulfide, bis(2-chloroethyl)sulfide, bis(2-chloroethylthio)methane, 1,2-bis(2-chloroethylthio)ethane, 1,3-bis(2-chloroethylthio)-n-propane, 1,4-bis(2-chloroethylthio)-n-butane, 1,5-bis(2-chloroethylthio)-n-pentane, bis(2-chloroethylthiomethyl) ether, bis(2-chloroethylthioethyl)ether, bis(2-chloroethyl)ethylamine, bis(2-chloroethyl) methylamine, saxitoxin, ricin, alkyl phosphonyldifluoride, alkyl phosphonites, chlorosarin, chlorosoman, amiton, 1,1,3,3,3-pentafluoro-2-(trifluoromethyl)-1-propene, 3-quinuclidinyl benzilate, methylphosphonyl dichloride, dimethyl methylphosphonate, dialkyl phosphoramidic dihalides, alkyl phosphoramidates, diphenyl hydroxyacetic acid, quinuclidin-3-ol, dialkyl aminoethyl-2-chlorides, dialkyl aminoethane-2-ols, dialkyl aminoethane-2-thiols, thiodiglycols, pinacolyl alcohols, phosgene, cyanogen chloride, hydrogen cyanide, chloropicrin, phosphorous oxychloride, phosphorous trichloride, phosphorus pentachloride, alkyl phosphorous oxychloride, alkyl phosphites, phosphorous trichloride, phosphorus pentachloride, alkyl phosphites, sulfur monochloride, sulfur dichloride, thionyl chloride, ethers, carbonyls, acetaldehyde, acetone, acrolein, acrylamide, acrylic acid, acrylonitrile, aldrin, dieldrin, ammonia, aniline, atrazine, benzidine, 2,3-benzofuran, beryllium, 1,1'-biphenyl, bis(2-chloroethyl)ether, bis(chloromethyl)ether, bromodichloromethane, bromoform, bromomethane, 1,3-butadiene, 1-butanol, 2-butanone, 2-butoxyethanol, butraldehyde, carbon disulfide, carbon tetrachloride, carbonyl sulfide, chlordane, chlordecone, mirex, chlorfenvinphos, chlorinated dibenzo-p-dioxins (CDDs), chlorine, chlorobenzene, chlorodibenzofurans (CDFs), chloroethane, chloroform, chloromethane, chlorophenols, chlorpyrifos, creosote, cresols, cyclohexane, DDT, DDE, DDD, DEHP, di(2-ethylhexyl)phthalate, diazinon, dibromochloropropane, 1,2-dibromoethane, 1,4-dichlorobenzene, 3,3'-dichlorobenzidine, 1,1-dichloroethane, 1,2-dichloroethane, 1,1-dichloroethene, 1,2-dichloroethene, 1,2-dichloropropane, 1,3-dichloropropene, dichlorvos, diethyl phthalate, diisopropyl methylphosphonate, di-n-butylphtalate, dimethoate, 1,3-dinitrobenzene, dinitrocresols, dinitrophenols, 2,4-dinitrotoluene, 2,6-dinitrotoluene, 1,2-diphenylhydrazine, di-n-octylphthalate (DNOP), 1,4-dioxane, dioxins, disulfoton, endosulfan, endrin, ethion, ethylbenzene, ethylene oxide, ethylene glycol, ethylparathion, fenthions, formaldehyde, freon 113, heptachlor, heptachlor epoxide, hexachlorobenzene, hexachlorobutadiene, hexachlorocyclohexane, hexachlorocyclopentadiene, hexachloroethane, hexamethylene diisocyanate, hexane, 2-hexanone, HMX (octogen), hydraulic fluids, hydrazines, hydrogen sulfide, iodine, isophorone, malathion, MBOCA, methamidophos, methanol, methoxychlor, 2-methoxyethanol, methyl ethyl ketone, methyl isobutyl ketone, methyl mercaptan, methylparathion, methyl t-butyl ether, methylchloroform, methylene chloride, methylenedianiline, methyl methacrylate, methyl-tert-butyl ether, mirex, chlordecone, monocrotophos, N-nitrosodimethylamine, N-nitrosodiphenylamine, N-nitrosodi-n-propylamine, naphthalene, nitrobenzene, nitrophenols, perchloroethylene, pentachlorophenol, phenol, phosphamidon, phosphorus, polybrominated biphenyls (PBBs), polychlorinated biphenyls (PCBs), polycyclic aromatic hydrocarbons (PAHs), propylene glycol, phthalic anhydride, pyrethrins, pyrethroids, pyridine, RDX (cyclonite), selenium, styrene, sulfur dioxide, sulfur trioxide, sulfuric acid, 1,1,2,2-tetrachloroethane, tetrachloroethylene, tetryl, thallium, tetrachloride, trichlorobenzene, 1,1,1-trichloroethane, 1,1,2-trichloroethane, trichloroethylene (TCE), 1,2,3-trichloropropane, 1,2,4-trimethylbenzene, 1,3,5-trinitrobenzene, 2,4,6-trinitrotoluene (TNT), vinyl acetate, and vinyl chloride; and
(A2) an active biological contaminant; and
(b) contacting the gas with aggregated particulates comprising cerium (IV) oxide and at least one other rare earth selected from the group consisting of lanthanum, cerium, praseodymium, neodymium, promethium, samarium, europium, gadolinium, terbium, dysprosium, holmium, erbium, thulium, ytterbium, lutetium, and mixtures thereof to remove the contaminant and provide a gas substantially depleted of the contaminant, wherein the at least one other rare earth has at least one of an oxidation state and valence state different from cerium (IV).

35. The method of claim 34, wherein the contaminant is a member of (A1) and wherein the aggregated particulates comprise at least about 75% by weight cerium (IV) oxide.

36. The method of claim 34, wherein the contaminant is a member of (A2) and wherein the aggregated particulates comprise at least about 75% by weight cerium (IV) oxide.

37. The method of claim 35, wherein each of the cerium (IV) oxide and the other rare earth remove contaminant (A1).

38. The method of claim 36, wherein each of the cerium (IV) oxide and the other rare earth remove the active biological contaminant.

39. The method of claim 34, wherein the cerium (IV) and at least one other rare earth have different oxidation states, wherein the aggregated particulates comprise rare earth-containing particles and a binder, wherein the rare earth-containing particles have a mean particle size of at least about 1 µm, and wherein the rare earth-containing particles comprise cerium (IV) oxide and lanthanum (III).

40. The method of claim 34, wherein the cerium (IV) oxide and the other rare earth comprise mixed valence states, wherein the aggregated particulates comprise rare earth-containing particles and a binder, wherein the rare earth-containing particles have a mean particle size of at least about 1 µm, and wherein the rare earth-containing particles comprise cerium (IV) oxide and lanthanum (III).

41. The method of claim 36, wherein the active biological contaminant comprises one or more of bacteria, fungi, protozoa, viruses, and algae.

42. The method of claim 25, wherein the active biological contaminant is one or more of *Entamoeba histolytica, Giardia*, and *Cryptosporidium parvum.*

43. The method of claim 25, wherein the active biological contaminant is algae.

44. The method of claim 1, wherein the one or more of a chemical and biological contaminant is the chemical contaminant.

45. The method of claim 1, wherein the one or more of a chemical and biological contaminant is the chemical contaminant and wherein the chemical contaminant is one or more of 1,1,3,3,3-pentafluoro-2-(trifluoromethyl)-1-propene, phosgene, acetone, acrolein, aldrin, dieldrin, 2,3-benzofuran, bis(2-chloroethyl)ether, bis(chloromethyl)ether, bromodichloromethane, bromoform, bromomethane, 2-butanone, butraldehyde, carbon tetrachloride, chlordane, chlordecone, mirex, chlorinated dibenzo-p-dioxins (CDDs), chlorobenzene, chlorodibenzofurans (CDFs), chloroethane, chloroform, chloromethane, DDT, DDE, DDD, DEHP, di(2-ethylhexyl)phthalate, dibromochloropropane, 1,2-dibromoethane, 1,4-dichlorobenzene, 1,1-dichloroethane, 1,2-dichloroethane, 1,1-dichloroethene, 1,2-dichloroethene, 1,2-dichloropropane, 1,3-dichloropropene, diethyl phthalate, di-n-butylphtalate, di-n-octylphthalate (DNOP), 1,4-dioxane, dioxins, endrin, ethylene oxide, formaldehyde, freon 113, heptachlor, heptachlor epoxide, hexachlorobenzene, hexachlorobutadiene, hexachlorocyclohexane, hexachlorocyclopentadiene, hexachloroethane, 2-hexanone, isophorone, methoxychlor, methyl ethyl ketone, methyl isobutyl ketone, methyl t-butyl ether, methylchloroform, methylene chloride, methyl methacrylate, methyl-tert-butyl ether, perchloroethylene, polybrominated biphenyls (PBBs), polychlorinated biphenyls (PCBs), phthalic anhydride, pyrethrins, pyrethroids, 1,1,2,2-tetrachloroethane, tetrachloroethylene, tetrachloride, trichlorobenzene, 1,1,1-trichloroethane, 1,1,2-trichloroethane, trichloroethylene (TCE), 1,2,3-trichloropropane, vinyl acetate, and vinyl chloride.

46. The method of claim 34, wherein the contaminant comprises one or more of bacteria, fungi, protozoa, viruses, and algae, wherein the aggregated particulates comprises cerium (IV) oxide and a lanthanum compound, and wherein the lanthanum compound has a different activity and effect compared to the cerium (IV) oxide.

* * * * *